US007285404B1

(12) United States Patent
Midoh et al.

(10) Patent No.: US 7,285,404 B1
(45) Date of Patent: Oct. 23, 2007

(54) CYCLIC DEPSIPEPTIDE SYNTHETASE AND METHOD FOR RECOMBINANT PRODUCTION

(75) Inventors: Naoki Midoh, Odawara (JP); Kaoru Okakura, Odawara (JP); Koichi Miyamoto, Odawara (JP); Manabu Watanabe, Odawara (JP); Koji Yanai, Odawara (JP); Tetsuya Yasutake, Odawara (JP); Sato Aihara, Odawara (JP); Takafumi Futamura, Odawara (JP); Horst Kleinkauf, Berlin (DE); Takeshi Murakami, Odawara (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 10/070,387

(22) PCT Filed: Sep. 7, 2000

(86) PCT No.: PCT/JP00/06103

§ 371 (c)(1),
(2), (4) Date: Mar. 6, 2002

(87) PCT Pub. No.: WO01/18179

PCT Pub. Date: Mar. 15, 2001

(30) Foreign Application Priority Data

Sep. 7, 1999 (JP) ................................ 11-253040
Apr. 6, 2000 (JP) ............................. 2000-104291

(51) Int. Cl.
*C12N 9/00* (2006.01)
(52) U.S. Cl. .................................................. 435/183
(58) Field of Classification Search ................ 435/189, 435/193
See application file for complete search history.

(56) References Cited

U.S. PATENT DOCUMENTS 5,763,221 A * 6/1998 Aoyagi et al. ............. 435/69.1
6,057,491 A * 5/2000 Cigan et al. ................ 800/279

FOREIGN PATENT DOCUMENTS

EP   382173       8/1990
EP   0 578 616 A2 * 12/1994
EP   780468       6/1997

OTHER PUBLICATIONS

Lawen et al. (1990) J Biol Chem 265:11355-11360.*
Branden et al. "Introduction to Protein Structure", Garland Publishing Inc. New York, 1991.*
Witkowski et al. (1999) Biochemistry 38:11643-11650.*
Matsudaira (1990) Methods Enzymol 182:602-613.*
Wozney (1990) Methods Enzymol 182:738-751.*
Database GenBank Accesssion No. S39842, Dec. 1993.*
Seffernick et al. (1999) J Bacteriol 183:2405-2410.*
Broun et al. (1998) Science 282:1315-1317.*
Guo et al. (2004) Proc Natl Acad Sci 101:9205-9210.*
Hult et al. (2003) Curr Opin Biotechnol 14:395-400.*
M Marahiel et al., "Modular Peptide Synthetases Involved in Nonribosomal Peptide Synthesis", Chemical Reviews, American Chemical Society, vol. 97, No. 7, Nov. 1997, pp. 2651-2673.
J. Burmester et al., "Highly Conserved N-Methyltransferases as an Integral part of Peptide Synthetases", Biochemistry and Molecular Biology International, vol. 37, No. 2, Oct. 1995, pp. 201-207.
Weckwerth, Wolfram et al., "Biosynthesis of PF1022A and Related Cyclooctadepsipeptides", The Journal of Biological Chemistry, Jun. 9, 2000, vol. 275, No. 23 pp. 17909-17915.
Haese, Angela et al., "Molecular characterization of the enniatin synthetase gene encoding a multifunctional enzyme catalysing N-methyldepsipeptide formation in *Fusarium scirpi*", Molecular Microbiology, Mar. 1993, vol. 7, No. 6, pp. 905-914.
Sasaki, Toru et al., "A new anthelmintic cyclodepsipeptide, PF1022A", The Journal of Anitbiotics, May 25, 1992, vol. 45, No. 5, pp. 692-697.

* cited by examiner

*Primary Examiner*—David J. Steadman
(74) *Attorney, Agent, or Firm*—Wenderoth, Lind & Ponack, L.L.P.

(57) ABSTRACT

The present invention provides an enzyme that synthesizes a cyclic depsipeptide, particularly the substance 1022, and a gene thereof. A cyclic depsipeptide synthetase according to the present invention comprises (a) an amino acid sequence of SEQ ID NO: 2 or (b) a modified amino acid sequence of the amino acid sequence of SEQ ID NO: 2 that have one or more modifications selected from a substitution, a deletion, an addition and an insertion and has cyclic depsipeptide synthetase activity. A cyclic depsipeptide synthetase gene according to the present invention comprises a nucleotide sequence encoding a cyclic depsipeptide synthetase. The present invention also provides a recombinant vector and a transformant for expressing the cyclic depsipeptide synthetase, and a mass production system for the cyclic depsipeptide. The present invention further provides a method for producing the cyclic depsipeptide synthetase.

4 Claims, 4 Drawing Sheets

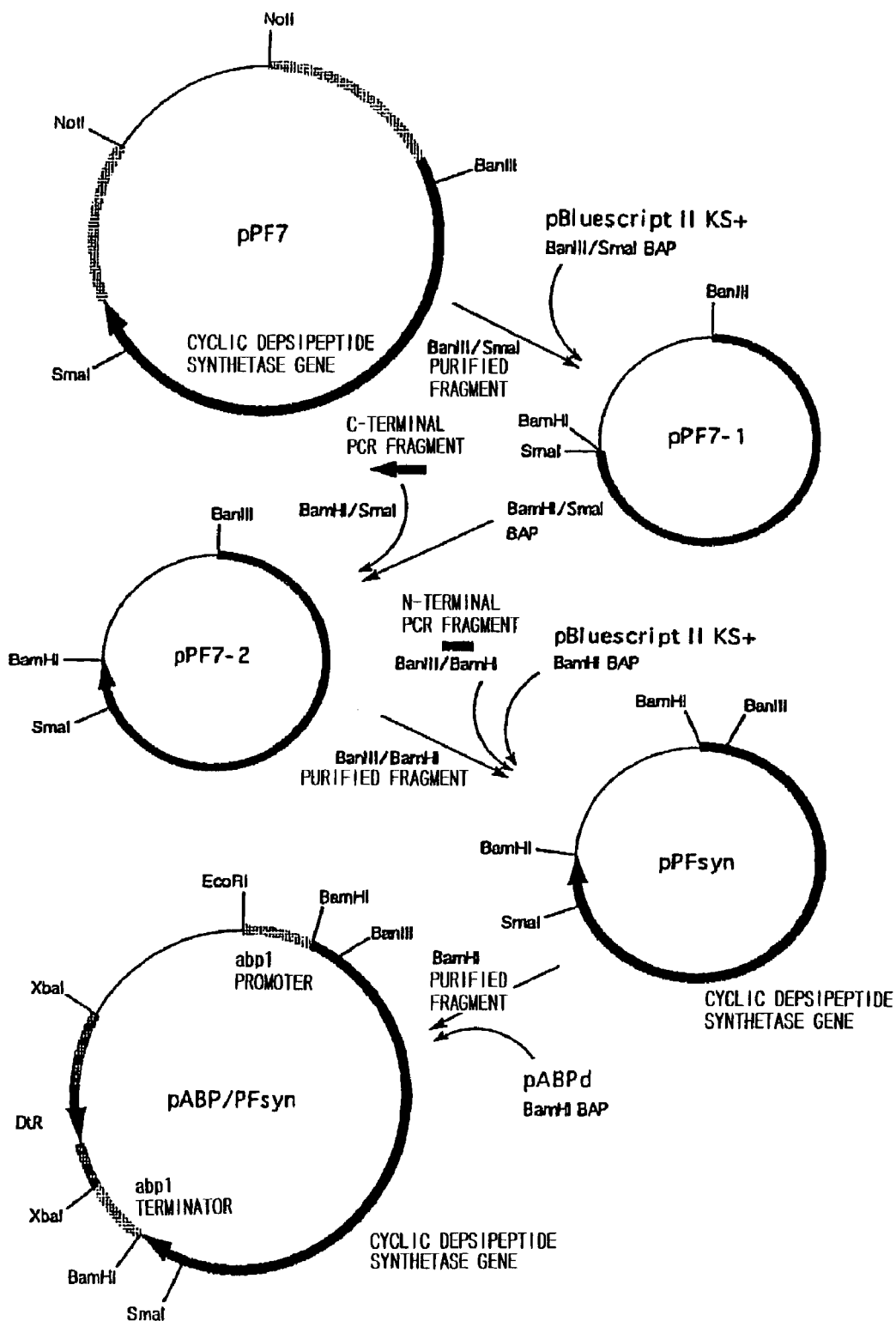
F I G. 1

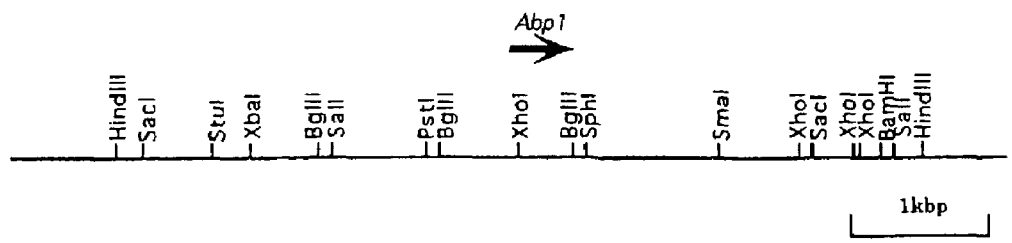
F I G. 2
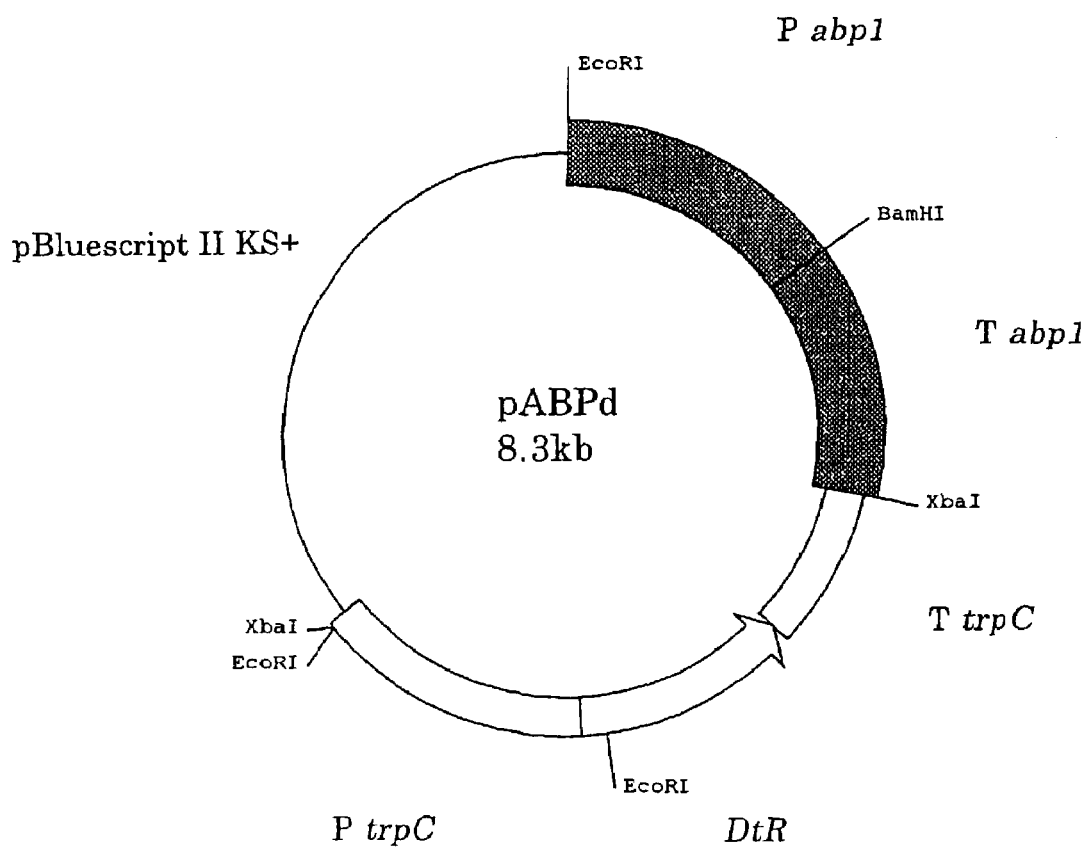
F I G. 3

US 7,285,404 B1

CYCLIC DEPSIPEPTIDE SYNTHETASE AND METHOD FOR RECOMBINANT PRODUCTION

This application is a 371 of PCT/JP00/06103 filed Sep. 7, 2000.

BACKGROUND OF THE INVENTION

1. Field of the Invention

The present invention relates to a cyclic depsipeptide synthetase and a gene thereof, and a mass production system for the cyclic depsipeptide. More specifically, the present invention relates to an enzyme for synthesizing substance PF1022 having anthelmintic activity and a gene thereof, and a mass production system for the substance PF1022.

2. Description of the Related Art

The substance PF1022 [cyclo(D-lactyl-L-N-methylleucyl-D-3-phenyllactyl-L-N-methylleucyl-D-lactyl-L-N-methylleucyl-D-3-phenyllactyl-L-N-methylleucyl)] is a cyclic depsipeptide which is produced by the filamentous fungus strain PF1022 (Mycelia sterilia, FERM BP-2671), which belongs to Agonomycetales, and has an extremely high anthelmintic activity against animal parasitic nematodes (Japanese Patent Application Laid-open No. 35796/1991; Sasaki, T. et al., J. Antibiotics, 45, 692, 1992). Accordingly, this substance is useful as a anthelmintic and also as a raw material for synthesizing a highly active derivative of this substance.

Generally, the amount of secondary metabolites produced by microorganisms isolated from nature is very small. Accordingly, in order to use the secondary metabolites industrially, it is necessary to improve the amount of the production. For this purpose, the culture method and the medium composition are investigated, fermentation conditions are improved by addition of precursors and the like, and strains are improved by mutation with UV irradiation or mutation inducers. Recently, in addition to these means, genetic recombination technology has become available to improve the productivity.

For example, enhancement of expression of an enzyme gene for biosynthesis, enhancement of expression of a regulatory gene for biosynthesis, and interruption of unnecessary biosynthesis pathways have been carried out (Khetan, A. and Hu, W.-S., Manual of Industrial Microbiology and Biotechnology, 2nd edition, p. 717, 1999). Furthermore, a known particular example is a method for increasing productivity in which a hemoglobin gene of a microorganism is expressed in order to enhance oxygen utilization ability (Minas, W. et al., Biotechnol. Prog., 14, 561, 1998).

In improving productivity using gene recombination technology, the most common technique is augmentation of expression of an enzyme gene for biosynthesis. To apply this technique, it is essential that a method of transforming a microorganism has been established, that a promoter and a terminator utilizable for expression augmentation are available, that the biosynthesis pathway has been elucidated, and that the related genes have been isolated. As to the substance PF1022-producing microorganism, a foreign gene has been successfully introduced by transformation (WO97/00944); however, the gene for biosynthesis has not been isolated.

The substance PF1022 comprises a structure in which L-N-methylleucine, D-lactic acid and D-phenyllactic acid are bonded via ester bonds and amide bonds. In a producing microorganism, it is synthesized by a certain kind of a peptide-synthesizing enzyme from four molecules of L-leucine, two molecules of D-lactic acid, and two molecules of D-phenyllactic acid. Peptide-synthesizing enzymes are those which carry out biosynthesis of secondary metabolites of microorganisms, such as peptides, depsipeptides, lipopeptides, and peptide lactone, using amino acids and hydroxy acids as a substrate. Sequences of some peptide-synthesizing enzymes have been already elucidated (Marahiel, M. A. et al., Chem. Rev., 97, 2651, 1997). The reaction by this type of enzyme is entirely different from that in a system of synthesizing a protein by a ribosome using mRNA as a template. It is thought that a peptide-synthesizing enzyme has one domain for each substrate and each substrate is activated by ATP in this domain and bonded via phosphopantothenic acid in the domain, and these then form amide bonds or ester bonds by a catalytic action in the regions between each domain.

SUMMARY OF THE INVENTION

An objective of the present invention is to provide an enzyme that synthesizes a cyclic depsipeptide, in particular the substance PF1022 (referred to as "cyclic depsipeptide synthetase" hereinafter).

Another objective of the present invention is to provide a gene that encodes the cyclic depsipeptide synthetase (referred to as "cyclic depsipeptide synthetase gene" hereinafter).

Still another objective of the present invention is to provide a recombinant vector and a transformant for expressing the cyclic depsipeptide synthetase, a mass-production system of the cyclic depsipeptide, and a method of producing the cyclic depsipeptide using the system.

Another objective of the present invention is to provide a method for producing the cyclic depsipeptide synthetase.

A cyclic depsipeptide synthetase according to the present invention is a protein comprising an amino acid sequence selected from the group consisting of the following sequences:

(a) an amino acid sequence of SEQ ID NO: 2, and
(b) a modified amino acid sequence of the amino acid sequence of SEQ ID NO: 2 that has one or more modifications selected from a substitution, a deletion, an addition and an insertion and has cyclic depsipeptide synthetase activity.

A cyclic depsipeptide synthetase gene according to the present invention comprises a nucleotide sequence encoding the cyclic depsipeptide synthetase.

Further, a cyclic depsipeptide synthetase gene according to the present invention comprises a nucleotide sequence selected from the group consisting of the following sequences:

(c) a DNA sequence of SEQ ID NO: 1,
(d) a nucleotide sequence that has at least 70% homology to the DNA sequence of SEQ ID NO: 1 and encodes a protein having cyclic depsipeptide synthetase activity,
(e) a modified DNA sequence of the DNA sequence of SEQ ID NO: 1 that has one or more modifications selected from a substitution, a deletion, an addition and an insertion and encodes a protein having cyclic depsipeptide synthetase activity, and
(f) a nucleotide sequence that hybridizes with the DNA sequence of SEQ ID NO: 1 under stringent conditions and encodes a protein having cyclic depsipeptide synthetase activity.

A recombinant vector according to the present invention comprises a cyclic depsipeptide synthetase gene according to the present invention.

A transformant and a mass-production system of the cyclic depsipeptide according to the present invention are a host comprising the recombinant vector according to the present invention.

A method for producing the cyclic depsipeptide according to the present invention comprises the steps of culturing the transformant according to the present invention and collecting the cyclic depsipeptide from the culture medium.

A method for producing a cyclic depsipeptide synthetase comprises the steps of culturing the transformant according to the present invention and collecting the cyclic depsipeptide synthetase from the culture medium.

According to the present invention, a cyclic depsipeptide synthetase can be excessively expressed in a substance PF1022-producing microorganism, and the substance PF1022 can be massively produced.

BRIEF DESCRIPTION OF THE DRAWINGS

FIG. 1 shows a construction procedure of plasmid pABP/PFsyn.

FIG. 2 shows a restriction map of a 6 kb HindIII fragment comprising the Abp1 gene.

FIG. 3 shows the construction and restriction map for pABPd.

DESCRIPTION OF THE PREFERRED EMBODIMENTS

Deposition of Microorganisms

Figure 4:
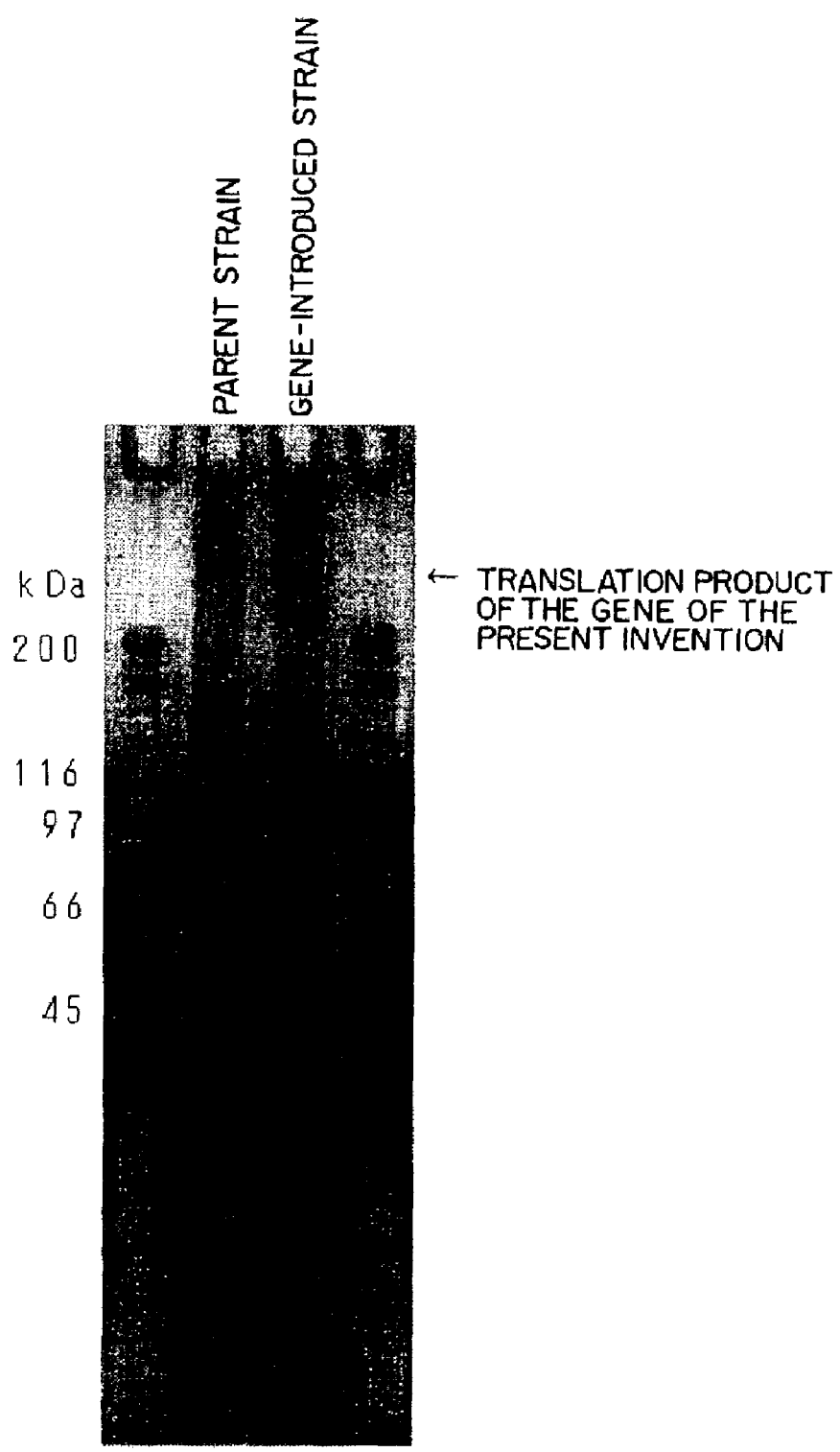
FIG. 4 shows the results of electrophoresis of the proteins extracted from the parent strain and a gene-introduced strain into which pABP/PFsyn is introduced.

The strain PF1022 described in Example 1-1 was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Jan. 24, 1989. The accession number is FERM BP-2671.

*Escherichia coli* (DH5α) transformed with plasmid pPFsyn described in Example 2-1-(1) was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 1, 1999. The accession number is FERM BP-7253.

*Escherichia coli* (DH5α) transformed with plasmid pPFsynN described in Example 2-1-(1) was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 1, 1999. The accession number is FERM BP-7254.

Gene and Protein

The present invention provides a cyclic depsipeptide synthetase, preferably a substance PF1022-synthesizing enzyme, and a gene thereof.

The enzyme according to the present invention acts on four molecules of L-leucine, two molecules of D-lactic acid, and two molecules of D-phenyllactic acid to synthesize substance PF1022. A derivative of substance PF1022 can be produced by in advance modifying D-lactic acid, L-leucine, and D-phenyllactic acid.

Examples of derivatives of substance PF1022 are derivatives in which two phenyl groups at the para positions in substance PF1022 are substituted by amino groups. In this case, for example, D-p-amino phenyllactic acid can be used instead of D-phenyllactic acid as a synthesizing substrate for the substance PF1022 derivative.

In sequence (b), the number of modifications can be, for example, one to several, more specifically, 1 to 6.

In sequence (e), the number of modifications can be, for example, one to dozens.

In sequence (b) and sequence (e), if multiple mutations are introduced, said mutations can be the same or different.

Sequence (d) can be preferably at least 80%, more preferably at least 90%, or most preferably at least 95% homology to the DNA sequence of SEQ ID NO: 1.

In sequence (f), the term "stringent conditions" means that a membrane after hybridization is washed at a high temperature in a solution of low salt concentration, for example, at a 0.2×SSC concentration (1×SSC: 15 mM trisodium citrate, 150 mM sodium chloride) in a 0.1% SDS solution at 60° C. for 15 minutes.

Whether sequence (b) "has the cyclic depsipeptide synthetase activity" or not can be evaluated, for example, by providing a substrate for the cyclic depsipeptide, reacting the protein to be tested, and then confirming the synthesis of the cyclic depsipeptide, for example, by chromatography.

Whether sequences (d), (e) and (f) "encode a protein having cyclic depsipeptide synthetase activity" or not can be evaluated, for example, by expressing the nucleotide sequence to be tested in a host, reacting the resulting protein with a substrate for the cyclic depsipeptide, and then confirming the synthesis of the cyclic depsipeptide, for example, by chromatography, as described in Example 2.

Given the amino acid sequence of a synthesizing enzyme of the present invention, nucleotide sequences encoding the amino acid sequence can be easily determined, and various nucleotide sequences encoding the amino acid sequence depicted in SEQ ID NO: 2 can be selected. Thus, nucleotide sequences encoding the synthesizing enzyme according to the present invention include any DNA sequence encoding the same amino acid sequence and having degenerative codons, in addition to a part or all of the DNA sequence of SEQ ID NO: 1, and further includes RNA sequences corresponding to those sequences.

A gene according to the present invention can be obtained, for example, based on the following.

A genomic DNA is isolated from a substance PF1022-producing microorganism and cleaved with appropriate restriction enzymes, and a library comprising the genomic DNA of the substance PF1022-producing microorganism is constructed using a phage vector. Appropriate primers are synthesized based on a conservative region of the amino acid sequence of the peptide-synthesizing enzyme or a partial amino acid sequence of the cyclic peptide-synthesizing enzyme purified from the substance PF1022-producing microorganism. The PCR method is carried out using the primers and the genomic DNA derived from the substance PF1022-producing microorganism as a template, and thus the DNA fragment of the cyclic peptide-synthesizing enzyme gene is amplified. The genomic library is screened using this DNA fragment as a probe. Thus, the whole region of the cyclic peptide-synthesizing enzyme gene can be isolated. After determining the nucleotide sequence of this DNA fragment, appropriate restriction enzyme cleavage sites are introduced upstream of the translation start codon and downstream of the translation stop codon by PCR or the like to obtain a gene fragment which contains the cyclic depsipeptide synthetase gene, exclusively.

Recombinant Vector

The present invention provides a recombinant vector comprising a nucleotide sequence encoding a cyclic depsipeptide synthetase.

The procedure and method for constructing a recombinant vector according to the present invention can be any of those commonly used in the field of genetic engineering.

Examples of the vector to be used in the present invention include vectors that can be incorporated into a host chromosome DNA and vectors having a self-replicable autonomous replication sequence which can be present as a plasmid in a host cell, for example, pUC vectors (e.g., pUC18 and pUC118), pBluescript vectors (e.g., pBluescriptII KS+), and pBR322 plasmid. One or more copies of the gene can be present in a host cell.

A recombinant vector according to the present invention can be constructed, for example, by operably ligating a promoter and a terminator upstream and downstream of the nucleotide sequence encoding a cyclic depsipeptide synthetase, respectively, and if appropriate, a gene marker and/or other regulatory sequences.

The ligation of the promoter and terminator to the gene according to the present invention and the insertion of the expression unit into the vector can be carried out by known methods.

A promoter and a terminator to be used in the present invention are not particularly limited. Examples of the promoter and the terminator include regulatory sequences of genes of glycolysis enzymes, such as 3-phosphoglycerate kinase, glycelaldehyde-3-phosphate dehydrogenase and enolase; regulatory sequences of amino acid-synthetase genes, such as ornithine carbamoyltransferase and tryptophan synthase; regulatory sequences of hydrolase genes, such as amylase, protease, lipase, cellulase, and acetamidase; regulatory sequences of genes of oxidation-reduction enzymes, such as nitrate reductase, orotidine-5'-phosphate dehydrogenase, and alcohol dehydrogenase; and a regulatory sequence of a gene derived from a substance PF1022-producing microorganism, such as Abp1, which is highly expressed in the substance PF1022-producing microorganism.

A protein of the present invention can be expressed as a fusion protein by ligating a gene according to the present invention to a foreign gene encoding a translation region of another protein.

A gene marker can be introduced, for example, by introducing an appropriate restriction enzyme cleaving site into a regulatory sequence by the PCR method, inserting this regulatory sequence into a plasmid vector, and ligating a selective marker gene such as a drug resistance gene and/or a gene complementing a nutritional requirement to the vector.

A gene marker can be appropriately selected depending on the technique for selecting a transformant. For example, a gene encoding drug resistance or a gene complementing a nutritional requirement can be used. Examples of the drug resistance gene include genes conferring resistance to destomycin, benomyl, oligomycin, hygromycin, G418, bleomycin, bialaphos, blastcidin S, phleomycin, phosphinothricin, ampicillin, and kanamycin. Examples of the gene complementing a nutritional requirement include amdS, pyrG, argB, trpC, niaD, TRP1, LEU2, URA3, and the like.

Production of Transformant and Cyclic Depsipeptide

The present invention provides a host transformed with the above-mentioned vector.

A host to be used in the present invention is, not particularly restricted, any microorganism which can be used as a host for genetic recombination. Examples of the host to be used include microorganisms, namely certain bacteria or fungi, preferably Escherichia coli, bacteria of genus Bacillus, actinomycetes, yeasts, and filamentous fungi, more preferably filamentous fungi which produce substance PF1022, most preferably the strain PF1022 (Mycelia sterilia, FERM BP-2671).

A recombinant vector for the gene expression can be introduced into a host by an ordinary method. Examples of the method for the introduction include the electroporation method, the polyethylene glycol method, the Agrobacterium method, the lithium method, and the calcium chloride method. A method most effective for a specific host cell can be selected. The polyethylene glycol method is preferable when a substance PF1022-producing microorganism is used as a host.

A transformant can be cultured by appropriately selecting a medium, culture conditions and the like according to an ordinary method. Conventional components can be used for a medium. As a carbon source, glucose, sucrose, cellulose, starch syrup, dextrin, starch, glycerol, molasses, animal and vegetable oils, and the like can be used. As a nitrogen source, soybean powder, wheat germ, pharma media, cornsteep liquor, cotton seed lees, bouillon, peptone, polypeptone, malt extract, yeast extract, ammonium sulfate, sodium nitrate, urea, and the like can be used. If necessary, inorganic salts which can produce sodium, potassium, calcium, magnesium, cobalt, chlorine, phosphoric acid, sulfuric acid, and other ions, such as potassium chloride, calcium carbonate, dipotassium hydrogenphosphate, magnesium sulfate, monopotassium phosphate, zinc sulfate, manganese sulfate, and copper sulfate, can be effectively added. If necessary, various vitamins such as thiamine (e.g., thiamine hydrochloride), amino acids such as glutamic acid (e.g., sodium glutamate) and asparagine (e.g., DL-asparagine), trace nutrients such as nucleotides, and selective drugs such as antibiotics can be added. Further, organic and inorganic substances to promote microbial growth and enhance cyclic depsipeptide production can be appropriately added.

The cultivation can be carried out by a shaking culture method under an aerobic condition, an agitation culture method with aeration, or an aerobic submerged culture method. In particular, an aerobic submerged culture method is most preferable. The pH of the medium is, for example, about 6 to 8. An appropriate culture temperature is 15° C. to 40° C. Most cells grow at about 26° C. to 37° C. Production of the cyclic depsipeptide synthetase and cyclic depsipeptide depends on a media, culture conditions, or a host used. However, the maximum accumulation can be attained generally in 2 to 25 days in any culture method.

The cultivation is terminated when the amount of the cyclic depsipeptide synthetase or cyclic depsipeptide in the medium reaches its peak, and the cyclic depsipeptide synthetase or cyclic depsipeptide is isolated from the culture and purified.

The cyclic depsipeptide synthetase or cyclic depsipeptide can be extracted and purified from the culture by any conventional separation method based on its properties, such as a solvent extraction method, an ion-exchange resin method, adsorption or distribution column chromatography, gel filtration, dialysis, precipitation, and crystallization, either singly or appropriately in combination.

The cyclic depsipeptide synthetase can be efficiently purified by hydrophobic chromatography using butyl agarose or the like.

The cyclic depsipeptide can be extracted from the culture, for example, with acetone, methanol, butanol, ethyl acetate, or butyl acetate. The cyclic depsipeptide can be further purified by chromatography using an adsorbent such as silica gel and aluminum, Sephadex LH-20 (Pharmacia), or Toyopearl HW-40 (Toso Co.). The pure cyclic depsipeptide can be obtained by using any of above-mentioned methods, either singly or appropriately in combination.

The present invention provides a mass production system of a cyclic depsipeptide. A host applicable to a cyclic depsipeptide production system, particularly a substance PF1022 production system, is preferably a substance PF1022-producing filamentous fungus, most preferably the strain PF1022 (*Mycelia sterilia*, FERM BP-2671). A recombinant vector used for transformation is preferably an expression vector in which a regulatory sequence (e.g., promoter and terminator), which functions in the substance PF1022-producing microorganism, is operably linked to a cyclic depsipeptide synthetase gene, most preferably an expression vector in which a regulatory sequence, which functions in the strain PF1022 (*Mycelia sterilia*, FERM BP-2671), is operably linked to a cyclic depsipeptide synthetase gene. A cyclic depsipeptide, particularly the substance PF1022, can be preferably produced by culturing a substance PF1022-producing microorganism transformed with an expression vector in which a regulatory sequence, which functions in the substance PF1022-producing microorganism, is operably linked to a cyclic depsipeptide synthetase gene, and isolating the cyclic depsipeptide from the culture.

In a host that does not synthesize any substrate for the substance PF1022, i.e., L-leucine, D-lactic acid or D-phenyllactic acid, the deficient substrate or a derivative thereof can be added to a culture medium to produce the substance PF1022 or a derivative thereof.

EXAMPLE

The present invention will now be illustrated in detail with reference to the following examples; however, these examples are not construed to limit the scope of the invention.

Example 1

Cloning of Cyclic Depsipeptide Synthetase Gene from Substance PF1022-Producing Microorganism 1. Isolation of Genomic DNA and Construction of Genomic Library The strain PF1022 (*Mycelia sterilia*, FERM BP-2671) was subjected to UV radiation or NTG treatment to induce mutation, and a genomic DNA was extracted from the resulting substance PF1022-producing strain 432-26, in which PF1022 productivity was improved. The substance PF1022-producing strain 432-26 was cultured in 50 ml of a seed medium (1% yeast extract, 1% malt extract, 2% polypeptone, 2.5% glucose, 0.1% dipotassium hydrogenphosphate, 0.05% magnesium sulfate, pH 7.0) at 26° C. for 2 days, and the cells were recovered by centrifugation. The cells thus obtained were frozen with liquid nitrogen and then smashed with a mortar and pestle. A genomic DNA was isolated from these smashed cells using ISOPLANT (Nippon Gene Co., Ltd.) according to the attached protocol. The isolated genomic DNA was partially digested with Sau3AI, after which a DNA fragment of 15 kb to 20 kb was recovered by agarose gel electrophoresis and treated with alkaline phosphatase to dephosphorylate the terminal of the DNA fragment. This DNA fragment was inserted into a phage vector, Lambda DASH II (Stratagene Co.). The recombinant phage vector thus obtained was subjected to in vitro packaging using a GigapackIII Gold Packaging Extract (Stratagene Co.) according to the attached protocol. Thereafter, *Escherichia coli* XL1-Blue MRA (P2) strain was infected with this recombinant phage and cultured on a plate to form a plaque.

2. Isolation of Partial DNA Fragment of Cyclic Depsipeptide Synthetase Gene

Multiple alignment of a known peptide-synthesizing enzyme was carried out, and well-conserved regions, WTSMYDG (SEQ ID NO: 3) and VVQYFPT (SEQ ID NO: 4) were found. Primers 5'-TGGACIWSNATGTAYGAYGG-3' (SEQ ID NO: 5) and 5'-GTIGGRAARTAYTGIACNAC-3' (SEQ ID NO: 6) were synthesized based on these sequences. Using these primers, PCR was carried out using the genomic DNA isolated from the substance PF1022-producing microorganism as a template. The PCR was conducted in 50 µl of reaction solution using 50 ng of the genomic DNA as a template, 1.25 units of ExTaq DNA polymerase (Takara Shuzo Co., Ltd.), attached buffer and dNTP Mixture, and 10 µM primer, under the following conditions: 3 minutes at 94° C.; 30 cycles of [one minute at 94° C., one minute at 65° C. (lowered 0.5° C. per cycle), one minute at 72° C.]; and 3 minutes at 72° C. A DNA fragment of about 350 bp was amplified by this reaction and this DNA fragment was inserted into plasmid vector pCR2.1 using an Original TA Cloning Kit (Invitrogen) according to the attached protocol.

The nucleotide sequence of the DNA fragment thus cloned was determined using a DNA Sequencing Kit dRhodamine Terminator Cycle Sequencing Ready Reaction (Applied Biosystems) and an ABI PRISM 310 Genetic Analyzer (Applied Biosystems) according to the attached protocol. Results revealed that the nucleotide sequence of the isolated DNA fragment was homologous to that of the peptide synthesizing enzyme gene, and was a part of the cyclic depsipeptide synthetase gene of interest.

3. Cloning of the Whole Region of Cyclic Depsipeptide Synthetase Gene

A probe used in the screening of the genomic library was prepared by incorporating fluorescein-labeled dUTP into a DNA fragment by PCR. The PCR was carried out in 50 µl of reaction solution using plasmid vector pCR2.1, into which 100 ng of the cyclic depsipeptide synthetase gene DNA fragment was inserted, as a template, 1.25 units of ExTaq DNA polymerase (Takara Shuzo, Co., Ltd.) and attached buffer, 0.2 mM dATP, 0.2 mM dCTP, 0.2 mM dGTP, 0.02 mM dTTP, 0.18 mM fluorescein-labeled dUTP (FluoroGreen, Amersham Pharmacia Biotech), and 10 µM primers (SEQ ID NO: 5 and SEQ ID NO: 6) under the following conditions: 2 minutes at 94° C.; 25 cycles of [30 seconds at 94° C., one minute at 55° C., one minute at 72° C.]; and 3 minutes at 72° C. A fluorescein-labeled probe of about 350 bp was constructed by this reaction.

A Hibond-N+ Membrane (Amersham Pharmacia Biotech) was placed on a plate with the plaque, which was prepared in Example 1-1, to adhere the plaque. The membrane was treated with alkaline, the recombinant phage DNA on the membrane was denatured into a single strand and adsorbed to the membrane. The membrane with the adsorbed phage DNA was taken into a buffer solution prepared using Hybridization Buffer Tablets (Amersham Pharmacia Biotech), and then incubation was carried out at 60° C. for 1 hour. The above-mentioned fluorescein-labeled probe was denatured by heat and added to this, and hybridization was carried out at 60° C. overnight. The membrane was then washed in a 1×SSC(SSC: 15 mM trisodium citrate, 150 mM sodium chloride)-0.1% SDS solution at 60° C. for 15 minutes, and further in a 0.2×SSC-0.1% SDS solution at 60° C. for 15 minutes. The fluorescein-bonded plaque was visualized using a DIG Wash and Block Buffer Set (Boehringer-Manheim), anti-fluorescein antibody labeled with alkaline phosphatase (Anti-fluorescein-AP, Fab fragment; Boehringer-Manheim), and nitroblue tetrazolium chloride (Boehringer-Manheim) and X-phosphate (Boehringer-Manheim) as coloring substrates, according to the attached protocol. In this way, a positive clone containing a 5' upstream region and a 3' downstream region homologous to the probe was selected.

4. Determination of Nucleotide Sequence

The DNA fragment in the positive clone thus isolated was amplified by PCR using phage vector sequences 5'-GCG-GAATTAACCCTCACTAAAGGGAACGAA-3' (SEQ ID NO: 7) and 5'-GCGTAATACGACTCACTATAGGGC-GAAGAA-3' (SEQ ID NO: 8) as primers. The PCR was carried out in 50 µl of reaction solution using 100 ng of the positive clone DNA as a template, 2.5 units of LA Taq DNA polymerase (Takara Shuzo Co., Ltd.), attached buffer and dNTP Mixture, 2.5 mM magnesium chloride, and 0.2 µM primers under the following conditions: one minute at 94° C.; 25 cycles of [10 seconds at 98° C., 15 minutes at 68° C.]; and 15 minutes at 72° C. The resulting PCR product was purified, treated with a nebulizer and randomly decomposed to 0.5 kb to 2.0 kb. The terminals of these fragments were blunted with T4 DNA polymerase and phosphorylated with T4 polynucleotide kinase, after which the resulting fragments were inserted into the EcoRV site of pT7Blue (Novagen, inc.) and introduced into *Escherichia coli* JM109 strain. The resulting 168 colonies were subjected to direct PCR using M13 Primer M4 (Takara Shuzo Co., Ltd.) and M13 Primer RV (Takara Shuzo Co., Ltd.). After purification, sequencing was carried out using M13 Primer M4 (Takara Shuzo Co., Ltd.) as a primer. The PCR was carried out in 50 µl of reaction solution using 1.25 units of ExTaq DNA polymerase (Takara Shuzo Co., Ltd.), attached buffer and dNTP Mixture, and 0.5 µM primers, under the following conditions: 4 minutes at 94° C.; 30 cycles of [30 seconds at 94° C., 30 seconds at 55° C., 2 minutes at 72° C.); and 3 minutes at 72° C. Sequencing was carried out using a DNA Sequencing Kit dRhodamine Terminator Cycle Sequencing Ready Reaction (Applied Biosystems) and an ABI PRISM 310 Genetic Analyzer (Applied Biosystems) according to the attached protocol.

From the result, regions where the analysis was not sufficient were amplified by PCR with primers newly designed based on already-analyzed nucleotide sequences, and after purification, sequencing was carried out using the primers used for the PCR. The nucleotide sequence of the 15606-bp DNA fragment in the positive clone was determined.

The analysis of this sequence revealed that a 9633-bp open reading frame (ORF) was present and that the protein extrapolated from this sequence had 3210 amino acid residues and was 354 kDa and homologous to peptide-synthesizing enzymes. The enniatin-synthesizing enzyme (S39842) showed the highest homology, namely 56%. The nucleotide sequence and the amino acid sequence of the ORF of the cyclic depsipeptide synthetase gene of the present invention thus isolated are shown in SEQ ID NO: 1 and SEQ ID NO: 2, respectively.

Example 2

Improvement of PF1022 Productivity by Excessive Expression of Cyclic Depsipeptide Synthetase Gene 1. Construction of Recombinant Vector for Gene Expression (FIG. 1)

(1) Cloning of Cyclic Depsipeptide Synthetase Gene Region

The inserted DNA fragment was cleaved with NotI from the positive clone obtained in Example 1-3, and inserted into the NotI site of pBluescriptII KS+ (Stratagene Co.) to construct plasmid pPF7. The pPF7 was cleaved with BanIII and SmaI, after which agarose gel electrophoresis was carried out and a DNA fragment of about 8250 bp was recovered from the agarose gel. This fragment was inserted into pBluescriptII KS+ to construct plasmid pPF7-1.

PCR was carried out using pPF7 as a template; 5'-AG-CATCGGATCCTAACAATGGGCGTTGAG-CAGCAAGCCCTA-3' (SEQ ID NO: 9, designed to start translation from Met on position 10 from the N-terminal of the ORF) or 5'-AGCATCGGATCCTAACAATGTCAAA-CATGGCACCACTCCCTA-3' (SEQ ID NO: 11, designed to start translation from Met on position 1 from the N-terminal of the ORF), and 5'-TTTGCTTCG-TACTCGGGTCCT-3' (SEQ ID NO: 10) as primers for the amplification of the fragment of about 440 bp (SEQ ID NO: 9 and SEQ ID NO: 10 were used) or the fragment of about 470 bp (SEQ ID NO: 11 and SEQ ID NO: 10 were used) from near the N-terminal to the BanIII site; and further, 5'-GCATCGCGATACTAGAGAAG-3' (SEQ ID NO: 12) and 5'-AGCATCGAATTCGGATCCCTAAAC-CAACGCCAAAGCCCGAAT-3' (SEQ ID NO: 13) as primers for the amplification of the fragment of about 920 bp from the SmaI site to the C-terminal. Here, the primers were designed to introduce BamHI sites to the 5' and 3' sides of the cyclic depsipeptide synthetase gene of the present invention. The PCR was carried out in 50 µl of reaction solution using 150 ng of plasmid DNA as a template, 2.5 units of KOD DNA polymerase (Toyobo Co., Ltd.) and attached buffer and dNTP Mixture, 1 mM magnesium chloride, and 0.5 µM primers, under the following conditions: 30 seconds at 98° C.; 10 cycles of [15 seconds at 98° C., 2 seconds at 65° C., 30 seconds at 74° C.]; and one minute at 74° C. The PCR reaction solution obtained using each primer was precipitated with ethanol to recover PCR products. The N-terminal region was cleaved with BamHI and BanIII, and the C-terminal region was cleaved with SmaI and BamHI, after which agarose gel electrophoresis was carried out to recover DNA fragments from the agarose gel.

The above-mentioned C-terminal region PCR fragment was inserted into the SmaI, BamHI sites of pPF7-1 to construct plasmid pPF7-2. This plasmid was cleaved with BanIII and BamHI, after which agarose gel electrophoresis was carried out to recover a DNA fragment of about 9170 bp from the agarose gel. This DNA fragment and the N-terminal region prepared using SEQ ID NO: 9 and SEQ ID NO: 10 were simultaneously inserted into the BamHI site of pBluescriptII KS+ to reconstruct the cyclic depsipeptide synthetase gene of the present invention, and thus plasmid pPFsyn (in which translation starts from Met on position 10 from the N-terminal of ORF) was constructed.

On the other hand, the DNA fragment of about 9170 bp cleaved from pPF7-2 and the N-terminal region constructed using SEQ ID NO: 9 and SEQ ID NO: 11 were simultaneously inserted into the BamHI site of pHSG299 (Takara Shuzo Co., Ltd.) to reconstruct the cyclic depsipeptide synthetase gene of the present invention, and thus plasmid pPFsynN (in which translation starts from Met on position 1 from the N-terminal of ORF) was constructed. In this way, the cyclic depsipeptide synthetase gene having BamHI sites on both terminals was constructed.

After cleaving pPFsyn or pPFsynN with BamHI, the cyclic depsipeptide synthetase gene region was each recovered from the gel.

(2) Construction of Expression Vector using Expression Regulatory Region of Abp1 Gene Isolation of Genomic DNA of Substance PF1022-Producing Microorganism The genomic DNA of the substance PF1022-producing microorganism (FERM BP-2671) was isolated according to the method of Horiuchi et al. (H. Horiuchi et al., J. Bacteriol., 170, 272-278, 1988). More specifically, cells of the substance PF1022-producing strain (FERM BP-2671) were cultured for 2 days in a seed medium (2.0% soluble starch, 1.0% glucose, 0.5% polypeptone, 0.6% wheat germ, 0.3% yeast extract, 0.2% soybean cake, and 0.2% calcium carbonate; pH 7.0 before sterilization; see Example 1 in WO97/00944), and the cells were recovered by centrifugation (3500 rpm, 10 minutes). The cells thus obtained were lyophilized, suspended in a TE solution, treated in a 3% SDS solution at 60° C. for 30 minutes, and then subjected to TE-saturated phenol extraction to remove the cell residue. The extract was precipitated with ethanol and treated with Ribonuclease A (Sigma) and Proteinase K (Wako Pure Chemical Industries, Ltd.), and the nucleic acid was then precipitated with 12% polyethylene glycol 6000. The precipitate was subjected to TE-saturated phenol extraction and ethanol precipitation, and the resulting precipitate was dissolved in a TE solution to obtain the genomic DNA.

Construction of Genomic Library of Substance PF1022-Producing Microorganism

The genomic DNA derived from the substance PF1022-producing microorganism prepared as described above was partially digested with Sau3AI. The product was ligated to the BamHI arm of a phage vector, a λEMBL3 Cloning kit (Stratagene Co.) using T4 ligase (Ligation Kit Ver. 2; Takara Shuzo Co., Ltd.). After ethanol precipitation, the precipitate was dissolved in a TE solution. The entire ligated mixture was used to infect *Escherichia coli* LE392 strain using a Gigapack III Plus Packaging kit (Stratagene Co.) to form phage plaques. The $1.3 \times 10^4$ ($2.6 \times 10^4$ PFU/ml) phage library obtained by this method was used for cloning of the Abp1 gene.

Cloning of the Abp1 Gene from the Genomic DNA Derived from Substance PF1022-Producing Microorganism A probe to be used was prepared by amplifying the translation region of the Abp1 gene by the PCR method. The PCR was carried out using the genomic DNA prepared from the substance PF1022-producing microorganism as described above as a template and synthetic primers 8-73U and 8-73R, according to a LETS GO PCR kit (SAWADY Technology). The PCR reaction for amplification was conducted by repeating 25 cycles of 30 seconds at 94° C., 30 seconds at 50° C., and 90 seconds at 72° C. DNA sequences of the 8-73U and 8-73R are as follows:

8-73U: CACAAACCAGGAACTCTTTC (SEQ ID NO: 14)

8-73R: GACATGTGGAAACCACATTTTG (SEQ ID NO: 15)

The PCR product thus obtained was labeled using an ECL Direct System (Amersham Pharmacia Biotech). The phage plaque prepared as described above was transferred to a Hibond N+ nylon transfer membrane (Amersham Pharmacia Biotech), and after alkaline denaturation, the membrane washed with 5-fold concentration SSC(SSC: 15 mM trisodium citrate, 150 mM sodium chloride), and dried to immobilize the DNA. According to the kit protocol, prehybridization (42° C.) was carried out for 1 hour, after which the previously labeled probe was added, and hybridization was carried out at 42° C. for 16 hours. The probe washed according to the kit protocol described above. The nylon membrane with the washed probe was immersed for one minute in a detection solution, and was then photosensitized on a medical X-ray film (Fuji Photo Film Co., Ltd.) to obtain one positive clone. Southern blot analysis of this clone showed that a HindIII fragment of at least 6 kb was identical with the restriction enzyme fragment of the genomic DNA. FIG. 2 shows the restriction map of this HindIII fragment. The HindIII fragment was subcloned into pUC119 to obtain pRQHin/119 for the following experiments.

Construction of Expression Vector

The promoter region and the terminator region of the Abp1 gene were amplified by the PCR method using pRQHin/119 as a template. The PCR was carried out using a PCR Super Mix High Fidelity (Lifetech Oriental Co., Ltd.), primers ABP-Neco and ABP-Nbam for promoter amplification and ABP-Cbam and ABP-Cxba for terminator amplification. The amplification reaction was conducted by repeating 25 cycles of 30 seconds at 94° C., 30 seconds at 50° C., and 90 seconds at 72° C. The DNA sequences of ABP-Neco, ABP-Nbam, ABP-Cbam and ABP-Cxba are as follows:

ABP-Neco: GGGGAATTCGTGGGTGGTGATAT-CATGGC (SEQ ID NO: 16)

ABP-Nbam: GGGGGATCCTTGATGGGTTTTGGG (SEQ ID NO: 17)

ABP-Cbam: GGGGGATCCTAAACTCCCATCTATAGC (SEQ ID NO: 18)

ABP-Cxba: GGGTCTAGACGACTCATTGCAGT-GAGTGG (SEQ ID NO: 19)

Each PCR product was purified with a Microspin S-400 column (Amersham Pharmacia Biotech) and precipitated with ethanol, after which the promoter was digested with EcoRI and BamHI, the terminator was digested with BamHI and XbaI, and the resulting fragments were ligated one by one to pBluescriptII KS+ previously digested with the same enzymes. The product was digested with XbaI, and a destomycin resistance cassette derived from pMKD01 (WO98/03667) was inserted to construct pABPd (FIG. 3). The pABPd has the promoter and the terminator of the Abp1 gene.

The cyclic depsipeptide synthetase gene region recovered from the gel as described above was inserted into the BamHI site of pABPd to construct expression vectors for the expression of the cyclic depsipeptide synthetase gene, i.e., pABP/PFsyn (in which translation starts from Met on position 10 from the N-terminal of ORF) and pABP/PFsynN (in which translation starts from Met on position 1 from the N-terminal of ORF).

2. Introduction of Cyclic Depsipeptide Synthetase Gene into Substance PF1022-Producing Microorganism, and Expression of the Gene The expression vector was introduced into the strain PF1022 (*Mycelia sterilia*, FERM BP-2671) according to the method described in Example 1 of WO97/00944, and strains having a high hygromycin B resistance were selected. The introduction of the gene of interest in these strains was verified by PCR using the primer 5'-TGATATGCTG-GAGCTTCCCT-3' (SEQ ID NO: 20) constructed from the sequence of the Abp1 promoter, and the primer 5'-GCA-CAACCTCTTTCCAGGCT-3' (SEQ ID NO: 21) constructed from the sequence of the cyclic depsipeptide synthetase gene. Thus, gene-introduced strains having a high hygromycin B resistance, into which the cyclic depsipeptide synthetase gene of the present invention was introduced, were selected.

The gene-introduced strains and the parent strain (*Mycelia sterilia*, FERM BP-2671) were each cultured in 50 ml of the seed medium at 26° C. for 2 days, after which a 1 ml portion of each resultant culture was inoculated into 50 ml of a production medium (6% starch syrup, 2.6% starch, 2% wheat germ, 1% pharma media, 0.2% magnesium sulfate heptahydrate, 0.2% calcium carbonate, and 0.3% sodium chloride; pH 7.5), and the cultivation was carried out at 26° C. for 4 days. The resulting culture was centrifuged at 4500 rpm for 5 minutes to recover the cells. The cells thus obtained were washed with 0.3 M potassium chloride, frozen with liquid nitrogen, and then lyophilized.

Figure 5:
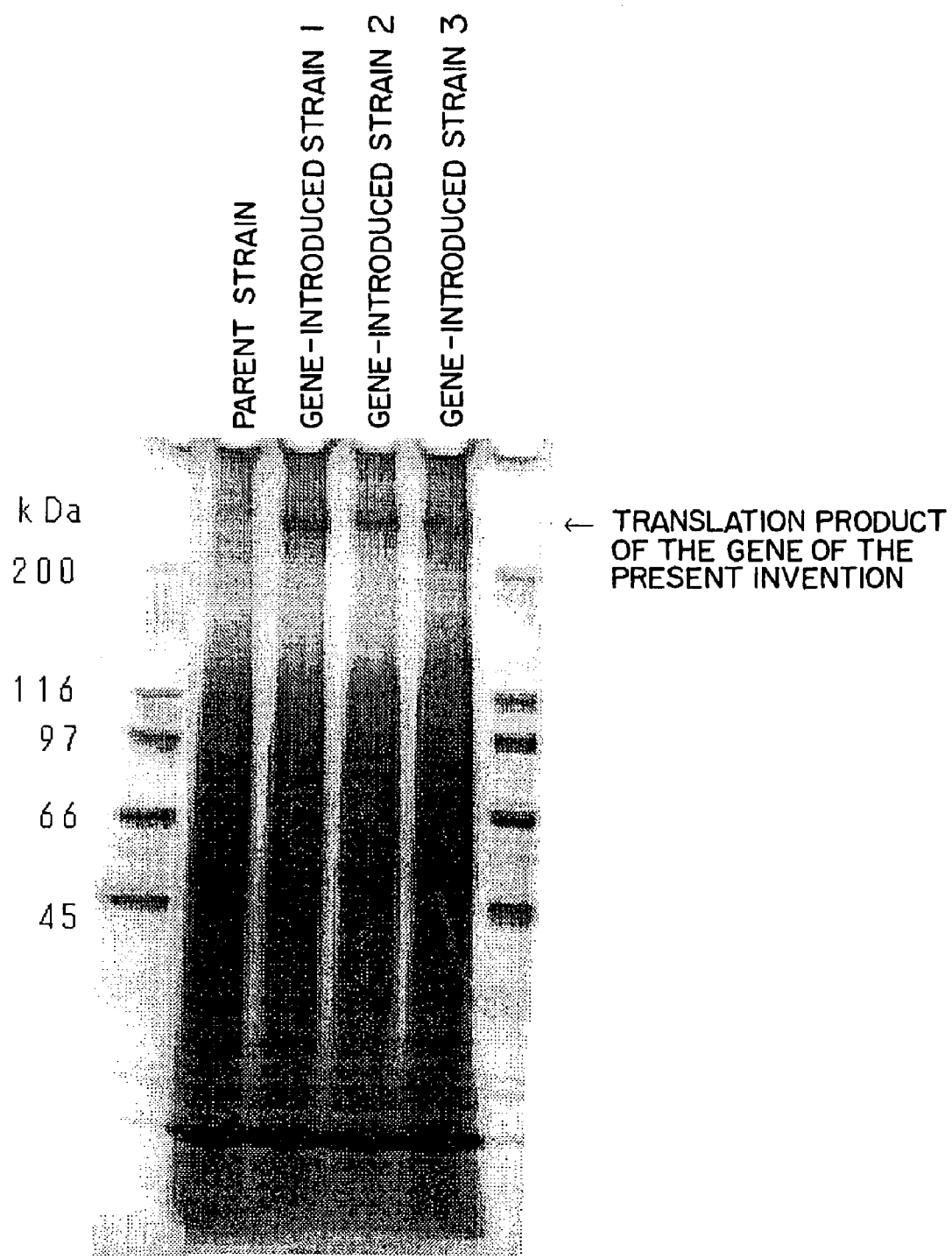
FIG. 5 shows the results of electrophoresis of the proteins extracted from the parent strain and a gene-introduced strain into which pABP/PFsynN is introduced.

The extraction procedure described below was carried out on ice or in a cold room at 4° C. The lyophilized cells (10 mg) and 1.0 ml of glass beads (0.5 mm in diameter) were placed in a 2 ml-microtube, and 1.0 ml of extraction buffer [50 mM Tris-HCl (pH8.0), 0.3 M potassium chloride, 60% glycerol, 10 mM ethylenediamine disodium tetraacetate, 5 mM dithiothreitol, 10 µM leupeptin, 1 mM phenylmethane-sulfonic acid, 60 µg/ml chymostatin] was added into the microtube. This microtube was set on a Mini-Bead Beater-8 (Biospeck) and extraction was carried out at the maximum speed for 3 minutes. After centrifugation at 15000 rpm for 5 minutes, 100 µl of supernatant was admixed with 100 µl of 10% trichloroacetic acid solution. After allowing to stand for 15 minutes, the admixture was centrifuged at 15000 rpm for 10 minutes, and the resultant precipitate was dissolved in 15 µl of an alkaline solution (2% sodium carbonate, 0.4% sodium hydroxide), and 60 µl of sample buffer [125 mM Tris-HCl (pH 6.8), 20% glycerol, 4% sodium dodecyl sulfate, 10% 2-mercapto ethanol, 50 mg/L Bromophenol Blue] was added. The resultant admixture was heated in boiling water for 5 minutes, and then subjected to electrophoresis with 4% to 20% polyacrylamide gels [sodium dodecyl sulfate-polyacrylamide gel electrophoresis (SDS-PAGE)] using an electrophoresis system (Tefco). After electrophoresis, the polyacrylamide gels were stained with Quick-CBB (Wako Pure Chemical Industries, Ltd.) according to the attached protocol. The result of the electrophoresis of the proteins extracted from the parent strain and the gene-introduced strain into which pABP/PFsyn was introduced is shown in FIG. 4. The result of the electrophoresis of the proteins extracted from the parent strain and the gene-introduced strains into which pABP/PFsynN was introduced is shown in FIG. 5.

Thus, the cyclic depsipeptide synthetase of the gene-introduced strains was much more highly expressed than that of the parent strain.

3. Extraction and Quantitative Measurement of Substance PF1022

The gene-introduced strains and the parent strain were each cultured in 50 ml of the seed medium at 26° C. for 2 days, after which a 1 ml portion of each culture was inoculated into 50 ml of the production medium, and the cultivation was carried out at 26° C. for 6 days. A 10 ml portion of each resulting culture was centrifuged at 3000 rpm for 10 minutes to recover the cells. Methanol (10 ml) was added to the cells, and the admixture was vigorously shaken and then allowed to stand for 30 minutes. The admixture was shaken again and centrifuged at 3000 rpm for 10 minutes, after which the substance PF1022 extracted from the cells of each strain in the supernatant was quantitatively measured by liquid chromatography. The column used was LiChrospher 100 RP-18 (e) (Kanto Kagaku), the column temperature was 40° C., the mobile phase was 80% acetonitrile, the flow rate was 1.0 ml/min, and the substance PF1022 was detected by adsorption at 210 nm. The retention time for the substance PF1022 was 5 to 6 minutes under these conditions. The experiment was repeated twice, and averages of the measurements of the substance PF1022 each extracted from the parent strain and the gene-introduced strain, into which pABP/PFsyn was introduced, are shown in Table 1.

TABLE 1

|  | Substance PF1022 (µg/ml) |
| --- | --- |
| Parent strain | 88 |
| Gene-introduced strain | 222 |

The gene-introduced strain showed about 2.5 times higher productivity than the parent strain. It was revealed that the substance PF1022 productivity was enhanced by excessively expressing the cyclic depsipeptide synthetase of the present invention.

Further, averages of the measurements of the substance PF1022 each extracted from the parent strain and the gene-introduced strains, into which pABP/PFsynN was introduced, are shown in Table 2.

TABLE 2

|  | Substance PF1022 (µg/ml) |
| --- | --- |
| Parent strain | 29 |
| Gene-introduced strain 1 | 123 |
| Gene-introduced strain 2 | 136 |
| Gene-introduced strain 3 | 172 |

The gene-introduced strains showed 4.3 to 6.0 times higher productivity than the parent strain. It was revealed that the productivity of substance PF1022 was enhanced by excessively expressing the cyclic depsipeptide synthetase of the present invention.

What is claimed is:

1. An isolated protein comprising the amino acid sequence of SEQ ID NO: 2.

2. A method for producing a protein having cyclo(D-lactyl-L-N-methylleucyl-D-3-phenyllactyl-L-N-methylleucyl-D-lactyl-L-N-methylleucyl-D-3-phenyllactyl-L-N-methylleucyl) (PF1022) synthetase activity, which comprises the steps of:
   culturing a host cell transformed with a vector containing a nucleotide sequence under conditions suitable for protein expression, wherein the nucleotide sequence is selected from the group consisting of:
   (a) a nucleotide sequence encoding the amino acid sequence of SEQ ID NO:2 and (b) the nucleotide sequence of SEQ ID NO:1; and collecting the protein from the culture medium.

3. An isolated protein encoded by a nucleotide sequence selected from the group consisting of:
   (a) a nucleotide sequence encoding the amino acid sequence of SEQ ID NO: 2; and
   (b) the nucleotide sequence of SEQ ID NO: 1.

4. A method for producing a protein having cyclo(D-lactyl-L-N-methylleucyl-D-3-phenyllactyl-L-N-methylleucyl-D-lactyl-L-N-methylleucyl-D-3-phenyllactyl-L-N-methylleucyl) (PF1022) synthetase activity, which comprises the steps of: culturing a host cell transformed with a vector containing a nucleotide sequence under conditions suitable for protein expression, wherein the nucleotide sequence is a nucleotide sequence that has at least 95% homology to the nucleotide sequence of SEQ ID NO:1 and which encodes a protein having PF1022 synthetase activity; and collecting the protein from the culture.

* * * * *

SEQUENCE LISTING

<160> NUMBER OF SEQ ID NOS: 21

<210> SEQ ID NO 1
<211> LENGTH: 9633
<212> TYPE: DNA
<213> ORGANISM: Mycelia sterilia
<220> FEATURE:
<221> NAME/KEY: CDS
<222> LOCATION: (1)..(9633)
<223> OTHER INFORMATION: peptide synthetase for PF1022
<220> FEATURE:
<221> NAME/KEY: mat_peptide
<222> LOCATION: (13)..(9630)

<400> SEQUENCE: 1

```
atg tca aac atg gca cca ctc cct acg atg ggc gtt gag cag caa gcc      48
Met Ser Asn Met Ala Pro Leu Pro Thr Met Gly Val Glu Gln Gln Ala
         -1   1               5                  10 cta tca ctt tca tgc ccc tta ctc cct cat gac gat gag aaa cac tca      96
Leu Ser Leu Ser Cys Pro Leu Leu Pro His Asp Asp Glu Lys His Ser
             15                  20                  25 gac aac ctt tac gag caa gca act cgg cac ttc ggc ttg agc cga gac     144
Asp Asn Leu Tyr Glu Gln Ala Thr Arg His Phe Gly Leu Ser Arg Asp
         30                  35                  40 aag atc gaa aat gtc tta cca tgt act tcc ttt caa tgt gat gtc ata     192
Lys Ile Glu Asn Val Leu Pro Cys Thr Ser Phe Gln Cys Asp Val Ile
 45                  50                  55                  60 gat tgc gcc gtc gac gat cgg cgg cat gct atc ggt cac gtc gtc tat     240
Asp Cys Ala Val Asp Asp Arg Arg His Ala Ile Gly His Val Val Tyr
                 65                  70                  75 gat atc ccc aat aca gtg gac atc cag cgt tta gcc gca gcc tgg aaa     288
Asp Ile Pro Asn Thr Val Asp Ile Gln Arg Leu Ala Ala Ala Trp Lys
             80                  85                  90 gag gtt gtg cgg cag aca cca atc ttg agg acc ggc atc ttt aca tca     336
Glu Val Val Arg Gln Thr Pro Ile Leu Arg Thr Gly Ile Phe Thr Ser
         95                 100                 105 gaa acc ggc gac tct ttt cag atc gtc ttg aaa gaa ggc tgc cta ccg     384
Glu Thr Gly Asp Ser Phe Gln Ile Val Leu Lys Glu Gly Cys Leu Pro
    110                 115                 120 tgg atg tac gcg aca tgt ctc ggc atg aag ggg gca gtg ata caa gat     432
Trp Met Tyr Ala Thr Cys Leu Gly Met Lys Gly Ala Val Ile Gln Asp
125                 130                 135                 140 gaa gca gtc gcc gct atg act gga ccg cgt tgc aat cga tat gtc gtc     480
Glu Ala Val Ala Ala Met Thr Gly Pro Arg Cys Asn Arg Tyr Val Val
                145                 150                 155 ctg gag gac ccg agt acg aag caa agg ctg ctc atc tgg aca ttc agc     528
Leu Glu Asp Pro Ser Thr Lys Gln Arg Leu Leu Ile Trp Thr Phe Ser
            160                 165                 170 cat gct tta gtg gat tat aca gtc cag gaa cgc atc ctt cag cgg gtt     576
His Ala Leu Val Asp Tyr Thr Val Gln Glu Arg Ile Leu Gln Arg Val
        175                 180                 185 ctc aca gta tac gac ggc cgg gac gtc gag tgc cct cgc atc aag gat     624
Leu Thr Val Tyr Asp Gly Arg Asp Val Glu Cys Pro Arg Ile Lys Asp
    190                 195                 200 aca gaa cat gtc tct cgg ttt tgg caa caa cac ttt gaa ggc tta gat     672
Thr Glu His Val Ser Arg Phe Trp Gln Gln His Phe Glu Gly Leu Asp
205                 210                 215                 220 gcc tcc gta ttt ccc ctt cta cca tct cac cta act gtg tgc aat ccc     720
Ala Ser Val Phe Pro Leu Leu Pro Ser His Leu Thr Val Cys Asn Pro
                225                 230                 235
```

```
aat gcg cgc gca gaa cat cat atc tca tac acg gga cca gtc cag agg      768
Asn Ala Arg Ala Glu His His Ile Ser Tyr Thr Gly Pro Val Gln Arg
        240                 245                 250 aag tgg tcc cat aca agt atc tgt cgg gct gca ctc gca gtt ctt cta      816
Lys Trp Ser His Thr Ser Ile Cys Arg Ala Ala Leu Ala Val Leu Leu
            255                 260                 265 tct cgc ttt aca cac tct tcg gag gcc ctc ttc ggt gtt gtg aca gaa      864
Ser Arg Phe Thr His Ser Ser Glu Ala Leu Phe Gly Val Val Thr Glu
270                 275                 280 caa tct cac aac tcc gag gac caa aga cgg tca att gat ggc ccc gca      912
Gln Ser His Asn Ser Glu Asp Gln Arg Arg Ser Ile Asp Gly Pro Ala
285                 290                 295                 300 agg aca gta gtg cct atc cgc gtc ctt tgt gcc cca gat caa tat gtg      960
Arg Thr Val Val Pro Ile Arg Val Leu Cys Ala Pro Asp Gln Tyr Val
                305                 310                 315 tcg gat gtc att ggg gca atc acc gca cac gaa cac gcc atg cgc ggg     1008
Ser Asp Val Ile Gly Ala Ile Thr Ala His Glu His Ala Met Arg Gly
                    320                 325                 330 ttt gag cac gct gga ctt cgc aat atc cgc cgt acc gga gac gac ggg     1056
Phe Glu His Ala Gly Leu Arg Asn Ile Arg Arg Thr Gly Asp Asp Gly
            335                 340                 345 tct gct gct tgt gga ttc cag acc gtg cta ctg gtg act gac ggt gat     1104
Ser Ala Ala Cys Gly Phe Gln Thr Val Leu Leu Val Thr Asp Gly Asp
350                 355                 360 gct ccc aag acc cct ggg agt gta ctt cat cga agt gta gaa gaa tcg     1152
Ala Pro Lys Thr Pro Gly Ser Val Leu His Arg Ser Val Glu Glu Ser
365                 370                 375                 380 gat aga ttc atg ccc tgc gct aat cgt gcc ctt ctg ctc gac tgc cag     1200
Asp Arg Phe Met Pro Cys Ala Asn Arg Ala Leu Leu Leu Asp Cys Gln
                385                 390                 395 atg gct ggc aac tcg gca tcc cta gtc gca cga tat gat cat aat gtg     1248
Met Ala Gly Asn Ser Ala Ser Leu Val Ala Arg Tyr Asp His Asn Val
                    400                 405                 410 atc gac cca cgc cag atg tct cgc ttc ctg cga cag cta gga tac ctg     1296
Ile Asp Pro Arg Gln Met Ser Arg Phe Leu Arg Gln Leu Gly Tyr Leu
            415                 420                 425 atc caa caa ttt cat cat cac gtc gat ctg cct ctg gtc aaa gaa ctg     1344
Ile Gln Gln Phe His His His Val Asp Leu Pro Leu Val Lys Glu Leu
430                 435                 440 gac gtc gtg acg gcg gag gat tgt gcg gaa atc gag aaa tgg aat tca     1392
Asp Val Val Thr Ala Glu Asp Cys Ala Glu Ile Glu Lys Trp Asn Ser
445                 450                 455                 460 gaa cgc cta aca atg caa gac gcc tta atc cac gac acc ata tcc aag     1440
Glu Arg Leu Thr Met Gln Asp Ala Leu Ile His Asp Thr Ile Ser Lys
                465                 470                 475 tgg gct gct ggc gat ccc aac aaa gct gca gtt ttc gct tgg gat ggg     1488
Trp Ala Ala Gly Asp Pro Asn Lys Ala Ala Val Phe Ala Trp Asp Gly
                    480                 485                 490 gaa tgg aca tac gcc gag cta gac aac ata tcc tcc cgt ctc gcc gtg     1536
Glu Trp Thr Tyr Ala Glu Leu Asp Asn Ile Ser Ser Arg Leu Ala Val
            495                 500                 505 tat atc caa tcc ctg gac ttg aga cca gga caa gca ata ctc cca ctc     1584
Tyr Ile Gln Ser Leu Asp Leu Arg Pro Gly Gln Ala Ile Leu Pro Leu
510                 515                 520 tgc ttc gag aag tca aaa tgg gtc gtc gcc aca att ctc gcc gtc ctc     1632
Cys Phe Glu Lys Ser Lys Trp Val Val Ala Thr Ile Leu Ala Val Leu
525                 530                 535                 540 aaa gtc ggt cgg gca ttc aca ctc atc gac ccg tgc gac ccc tcg gca     1680
Lys Val Gly Arg Ala Phe Thr Leu Ile Asp Pro Cys Asp Pro Ser Ala
                545                 550                 555
```

```
agg atg gcc cag gtc tgt cag cag acc tcc gcc aca gtc gct ctc acc      1728
Arg Met Ala Gln Val Cys Gln Gln Thr Ser Ala Thr Val Ala Leu Thr
            560                 565                 570 tcc aaa ctc cac aac acc acc tta cgt tcc gtc gtt tcc cgc tgc att      1776
Ser Lys Leu His Asn Thr Thr Leu Arg Ser Val Val Ser Arg Cys Ile
        575                 580                 585 gtg gtc gac gac gac ctc ctt cgg tcc tta ccc cac gcc gat ggc cgc      1824
Val Val Asp Asp Asp Leu Leu Arg Ser Leu Pro His Ala Asp Gly Arg
    590                 595                 600 tta aag gcc acc gtg aag cca cag gac ttg gcc tat gtt att ttc aca      1872
Leu Lys Ala Thr Val Lys Pro Gln Asp Leu Ala Tyr Val Ile Phe Thr
605                 610                 615                 620 tct ggc agc aca gga gag ccg aaa ggc atc atg atc gaa cat cgg ggg      1920
Ser Gly Ser Thr Gly Glu Pro Lys Gly Ile Met Ile Glu His Arg Gly
            625                 630                 635 ttc gtg tcg tgt gct atg aaa ttt ggc ccc gcg ctc gga atg gat gag      1968
Phe Val Ser Cys Ala Met Lys Phe Gly Pro Ala Leu Gly Met Asp Glu
        640                 645                 650 cac acg cgc gct ctt caa ttc gcc tca tat gcg ttt ggc gct tgt ctg      2016
His Thr Arg Ala Leu Gln Phe Ala Ser Tyr Ala Phe Gly Ala Cys Leu
    655                 660                 665 gta gaa gtt gtg aca gct ctg atg cac ggc ggc tgc gtc tgc atc cct      2064
Val Glu Val Val Thr Ala Leu Met His Gly Gly Cys Val Cys Ile Pro
670                 675                 680 tcc gat gac gat cgc ttg aac aat gta ccg gag ttc atc aaa agg gcc      2112
Ser Asp Asp Asp Arg Leu Asn Asn Val Pro Glu Phe Ile Lys Arg Ala
685                 690                 695                 700 cag gtg aac tgg gtg ata ctc act ccg tcg tat atc ggg aca ttc cag      2160
Gln Val Asn Trp Val Ile Leu Thr Pro Ser Tyr Ile Gly Thr Phe Gln
            705                 710                 715 ccg gaa gat gtc cct gga cta caa aca ctg gta ttg gtt gga gaa cct      2208
Pro Glu Asp Val Pro Gly Leu Gln Thr Leu Val Leu Val Gly Glu Pro
        720                 725                 730 atc tca gcg tct att cgg gat acc tgg gcc tcc cag gtt cga ctc ctg      2256
Ile Ser Ala Ser Ile Arg Asp Thr Trp Ala Ser Gln Val Arg Leu Leu
    735                 740                 745 aat gcc tac ggt cag agt gaa agc tca act atg tgc agc gtc acg gaa      2304
Asn Ala Tyr Gly Gln Ser Glu Ser Ser Thr Met Cys Ser Val Thr Glu
750                 755                 760 gtc agc ccg ctc tcc ctc gaa ccg aac aat atc ggt cgg gct gta ggc      2352
Val Ser Pro Leu Ser Leu Glu Pro Asn Asn Ile Gly Arg Ala Val Gly
765                 770                 775                 780 gca cga tcc tgg atc att gat ccc gac gag cct gat cgt ctt gct cca      2400
Ala Arg Ser Trp Ile Ile Asp Pro Asp Glu Pro Asp Arg Leu Ala Pro
            785                 790                 795 att ggc tgc att gga gag cta gtg atc gaa agt ccg ggc att gcg cgc      2448
Ile Gly Cys Ile Gly Glu Leu Val Ile Glu Ser Pro Gly Ile Ala Arg
        800                 805                 810 gac tat atc atc gcg ccg ccg ccg gac aag tcc ccc ttt ctc cta gca      2496
Asp Tyr Ile Ile Ala Pro Pro Pro Asp Lys Ser Pro Phe Leu Leu Ala
    815                 820                 825 ccc ccg gcc tgg tat cca gcc ggg aaa tta tcc aac gcc ttt aaa ttt      2544
Pro Pro Ala Trp Tyr Pro Ala Gly Lys Leu Ser Asn Ala Phe Lys Phe
830                 835                 840 tac aag act gga gat ctc gtg cgt tat gga cct gac ggc acc atc gtc      2592
Tyr Lys Thr Gly Asp Leu Val Arg Tyr Gly Pro Asp Gly Thr Ile Val
845                 850                 855                 860 tgc ctg gga cgc aaa gat tcg caa gtg aag atc cga ggg cag cgc gta      2640
Cys Leu Gly Arg Lys Asp Ser Gln Val Lys Ile Arg Gly Gln Arg Val
```

-continued

| | |
|---|---|
| gag atc agc gca gtg gaa gcc agt cta cga cga caa cta cct agt gac<br>Glu Ile Ser Ala Val Glu Ala Ser Leu Arg Arg Gln Leu Pro Ser Asp<br>     865              870              875<br>            880               885              890 | 2688 |
| atc atg ccc gtg gcc gaa gct atc aaa cgc tcg gat tcg tca ggc agc<br>Ile Met Pro Val Ala Glu Ala Ile Lys Arg Ser Asp Ser Ser Gly Ser<br>          895               900              905 | 2736 |
| aca gtc ttg act gcc ttc ttg ata ggg tca tct aag agc gga gat ggt<br>Thr Val Leu Thr Ala Phe Leu Ile Gly Ser Ser Lys Ser Gly Asp Gly<br>       910             915            920 | 2784 |
| aat ggc cac gct tta tct gcg gca gac gcc gtt atc ttg gat cac ggt<br>Asn Gly His Ala Leu Ser Ala Ala Asp Ala Val Ile Leu Asp His Gly<br>925              930              935              940 | 2832 |
| gct acc aac gag ata aac gcg aag ttg cag caa atc ctt ccc cag cat<br>Ala Thr Asn Glu Ile Asn Ala Lys Leu Gln Gln Ile Leu Pro Gln His<br>             945              950              955 | 2880 |
| tcc gtt cca tcc tat tat atc cac atg gaa aat ctt cct cga act gcc<br>Ser Val Pro Ser Tyr Tyr Ile His Met Glu Asn Leu Pro Arg Thr Ala<br>       960              965              970 | 2928 |
| acc ggc aaa gcg gac agg aaa atg ctt cga tct att gct agc aag cta<br>Thr Gly Lys Ala Asp Arg Lys Met Leu Arg Ser Ile Ala Ser Lys Leu<br>          975               980              985 | 2976 |
| ttg ggt gaa ttg tct cag aac gtg aca tct caa ccg att gag aag cac<br>Leu Gly Glu Leu Ser Gln Asn Val Thr Ser Gln Pro Ile Glu Lys His<br>     990             995            1000 | 3024 |
| gat gcc cca gca act ggt ata gag gtc aag ctg aag gag ctt tgg ttt<br>Asp Ala Pro Ala Thr Gly Ile Glu Val Lys Leu Lys Glu Leu Trp Phe<br>1005            1010            1015            1020 | 3072 |
| ctg agc ttg aat ctt aat ccc aac tct caa gat gtc gga gcg agt ttc<br>Leu Ser Leu Asn Leu Asn Pro Asn Ser Gln Asp Val Gly Ala Ser Phe<br>            1025            1030            1035 | 3120 |
| ttt gac tta ggc gga aat tcc att atc gcc atc aaa atg gta aac atg<br>Phe Asp Leu Gly Gly Asn Ser Ile Ile Ala Ile Lys Met Val Asn Met<br>        1040            1045            1050 | 3168 |
| gcg agg tca gct ggg ata gca ctg aag gta tcc gac ata ttc cag aat<br>Ala Arg Ser Ala Gly Ile Ala Leu Lys Val Ser Asp Ile Phe Gln Asn<br>     1055            1060            1065 | 3216 |
| ccc acg ctc gcc ggc ctt gtg gat gtc atc ggg cga gac ccg gct ccg<br>Pro Thr Leu Ala Gly Leu Val Asp Val Ile Gly Arg Asp Pro Ala Pro<br>1070            1075            1080 | 3264 |
| tac aac ctc atc cca aca aca gca tac agc gga cct gtt gag cag tcg<br>Tyr Asn Leu Ile Pro Thr Thr Ala Tyr Ser Gly Pro Val Glu Gln Ser<br>1085            1090            1095            1100 | 3312 |
| ttc gcc cag ggc cgt cta tgg ttc ttg gac cag atc gaa ctc gat gcg<br>Phe Ala Gln Gly Arg Leu Trp Phe Leu Asp Gln Ile Glu Leu Asp Ala<br>            1105            1110            1115 | 3360 |
| ttg tgg tac ctt cta cca tac gcc gtt cgc atg cgc ggg cca ttg cat<br>Leu Trp Tyr Leu Leu Pro Tyr Ala Val Arg Met Arg Gly Pro Leu His<br>        1120            1125            1130 | 3408 |
| att gat gcg ctc act att gcg ttg cta gct ata cag caa cga cat gaa<br>Ile Asp Ala Leu Thr Ile Ala Leu Leu Ala Ile Gln Gln Arg His Glu<br>     1135            1140            1145 | 3456 |
| acc ttg cgg aca acc ttt gag gag cag gac ggc gta ggc gtt cag gtt<br>Thr Leu Arg Thr Thr Phe Glu Glu Gln Asp Gly Val Gly Val Gln Val<br>1150            1155            1160 | 3504 |
| gtc cat gcg agc ccc atc tcc gac ttg agg ata atc gac gta tca ggc<br>Val His Ala Ser Pro Ile Ser Asp Leu Arg Ile Ile Asp Val Ser Gly<br>1165            1170            1175            1180 | 3552 |
| gac cga aac agt gac tac ctc cag ttg cta cac caa gag cag acg act | 3600 |

```
Asp Arg Asn Ser Asp Tyr Leu Gln Leu Leu His Gln Glu Gln Thr Thr
            1185                1190                1195 cca ttc att cta gca tgt cag gca gga tgg agg gta tca ctg att aga       3648
Pro Phe Ile Leu Ala Cys Gln Ala Gly Trp Arg Val Ser Leu Ile Arg
        1200                1205                1210 cta gga gaa gat gat cac atc ctc tct atc gta atg cat cac atc atc       3696
Leu Gly Glu Asp Asp His Ile Leu Ser Ile Val Met His His Ile Ile
            1215                1220                1225 tcc gac ggc tgg tct atc gac att cta cgc cgg gaa cta agc aat ttc       3744
Ser Asp Gly Trp Ser Ile Asp Ile Leu Arg Arg Glu Leu Ser Asn Phe
        1230                1235                1240 tat tca gcc gct ctc cgg ggc tct gat cct cta tcg gtg gtg agc cca       3792
Tyr Ser Ala Ala Leu Arg Gly Ser Asp Pro Leu Ser Val Val Ser Pro
1245                1250                1255                1260 ctc cca ctc cac tac cgc gac ttt tcc gtt tgg caa aag cag gtc gaa       3840
Leu Pro Leu His Tyr Arg Asp Phe Ser Val Trp Gln Lys Gln Val Glu
            1265                1270                1275 cag gag acc gaa cat gag cgg caa ctc gaa tac tgg gtc aag cag ctc       3888
Gln Glu Thr Glu His Glu Arg Gln Leu Glu Tyr Trp Val Lys Gln Leu
        1280                1285                1290 gca gac agc tcg gcc gcc gaa ttc cta acc gac ttc ccc cga ccc aac       3936
Ala Asp Ser Ser Ala Ala Glu Phe Leu Thr Asp Phe Pro Arg Pro Asn
    1295                1300                1305 ata ctg tcc ggt gaa gca ggt tcc gtc cca gtg acg atc gaa ggc gaa       3984
Ile Leu Ser Gly Glu Ala Gly Ser Val Pro Val Thr Ile Glu Gly Glu
1310                1315                1320 ctg tat gaa agg ctc caa gaa ttc tgt aaa gta gag caa atg acg cct       4032
Leu Tyr Glu Arg Leu Gln Glu Phe Cys Lys Val Glu Gln Met Thr Pro
1325                1330                1335                1340 ttc gcc gtg ttg tta ggg gcc ttc cgc gcg acc cat tat cgt ctc acc       4080
Phe Ala Val Leu Leu Gly Ala Phe Arg Ala Thr His Tyr Arg Leu Thr
            1345                1350                1355 ggc gcc gaa gac tcg atc atc ggc acg ccc atc gcg aac cgc aac cgc       4128
Gly Ala Glu Asp Ser Ile Ile Gly Thr Pro Ile Ala Asn Arg Asn Arg
        1360                1365                1370 cag gag ctt gaa aac atg atc ggc ttc ttc gtc aac acc caa tgc atg       4176
Gln Glu Leu Glu Asn Met Ile Gly Phe Phe Val Asn Thr Gln Cys Met
    1375                1380                1385 cga atc acg gtc gac ggc gac gac act ttt gaa agc ctg gtg cga caa       4224
Arg Ile Thr Val Asp Gly Asp Asp Thr Phe Glu Ser Leu Val Arg Gln
1390                1395                1400 gtt cgg acc acg gcg acg gcg gca ttc gag cac caa gac gtc ccc ttt       4272
Val Arg Thr Thr Ala Thr Ala Ala Phe Glu His Gln Asp Val Pro Phe
1405                1410                1415                1420 gag cgc gtc gtg acg gca ctc ctt cca cgc tcg aga gac cta tcc cga       4320
Glu Arg Val Val Thr Ala Leu Leu Pro Arg Ser Arg Asp Leu Ser Arg
            1425                1430                1435 aac cca cta gca cag ctc acc ttc gct ctt cat tct caa cag gac ctc       4368
Asn Pro Leu Ala Gln Leu Thr Phe Ala Leu His Ser Gln Gln Asp Leu
        1440                1445                1450 ggc aag ttc gag ctg gag ggt ctc gta gcg gaa ccc gtc tcg aac aag       4416
Gly Lys Phe Glu Leu Glu Gly Leu Val Ala Glu Pro Val Ser Asn Lys
    1455                1460                1465 gta tac acc agg ttc gac gtg gag ttt cac ctg ttc caa gaa gcc gga       4464
Val Tyr Thr Arg Phe Asp Val Glu Phe His Leu Phe Gln Glu Ala Gly
1470                1475                1480 aga cta agc ggt aac gtg gca ttt gcg gca gat cta ttc aag cct gag       4512
Arg Leu Ser Gly Asn Val Ala Phe Ala Ala Asp Leu Phe Lys Pro Glu
1485                1490                1495                1500
```

-continued

| | |
|---|---|
| acc att agc aat gta gtc gcc ata ttt ttc caa atc ctg cga caa ggc<br>Thr Ile Ser Asn Val Val Ala Ile Phe Phe Gln Ile Leu Arg Gln Gly<br>                  1505                    1510                  1515 | 4560 |
| att cgc cag cct cgg act cca atc gct gtt ctc ccg ctt acc gat ggg<br>Ile Arg Gln Pro Arg Thr Pro Ile Ala Val Leu Pro Leu Thr Asp Gly<br>1520                    1525                    1530 | 4608 |
| tta gcg gac ctt cgt gcc atg ggc ttg ctt gag atc gag aag gca gaa<br>Leu Ala Asp Leu Arg Ala Met Gly Leu Leu Glu Ile Glu Lys Ala Glu<br>                  1535                    1540                  1545 | 4656 |
| tac ccg cgg gag tcg agc gtc gtc gac gtc ttc cgc aag cag gtg gcc<br>Tyr Pro Arg Glu Ser Ser Val Val Asp Val Phe Arg Lys Gln Val Ala<br>                  1550                    1555                  1560 | 4704 |
| gct cac ccg cac gct ttt gcc gtt gtc gat tcg gca tcg cgc ctc aca<br>Ala His Pro His Ala Phe Ala Val Val Asp Ser Ala Ser Arg Leu Thr<br>1565                    1570                    1575                  1580 | 4752 |
| tat gct gat ctc gat cgt caa tcc gat caa ctc gcg acc tgg ctc ggt<br>Tyr Ala Asp Leu Asp Arg Gln Ser Asp Gln Leu Ala Thr Trp Leu Gly<br>                  1585                    1590                  1595 | 4800 |
| cgg cgc aat atg acg gct gag acg ctg gtc ggg gtg tta gca ccg cgg<br>Arg Arg Asn Met Thr Ala Glu Thr Leu Val Gly Val Leu Ala Pro Arg<br>                  1600                    1605                  1610 | 4848 |
| tca tgt caa aca gtt gtt gcc att tta ggt atc ctg aaa gcg aat ctc<br>Ser Cys Gln Thr Val Val Ala Ile Leu Gly Ile Leu Lys Ala Asn Leu<br>                  1615                    1620                  1625 | 4896 |
| gca tat ctc ccg ctt gat gtg aat tgt cct acc gcc cgc ctg caa aca<br>Ala Tyr Leu Pro Leu Asp Val Asn Cys Pro Thr Ala Arg Leu Gln Thr<br>                  1630                    1635                  1640 | 4944 |
| atc cta tct aca ttg aat cgg cac aag ttg gtc cta ctc ggc tct aac<br>Ile Leu Ser Thr Leu Asn Arg His Lys Leu Val Leu Leu Gly Ser Asn<br>1645                    1650                    1655                  1660 | 4992 |
| gca act act ccg gat gtc cag ata cct gat gta gag ctg gta cga atc<br>Ala Thr Thr Pro Asp Val Gln Ile Pro Asp Val Glu Leu Val Arg Ile<br>                  1665                    1670                  1675 | 5040 |
| agc gat atc tta gat cgc ccc atc aat ggc cag gca aag cta aat ggt<br>Ser Asp Ile Leu Asp Arg Pro Ile Asn Gly Gln Ala Lys Leu Asn Gly<br>                  1680                    1685                  1690 | 5088 |
| cat aca aaa tcg aat ggc tac tca aag cca aac ggc tat acg cat ctg<br>His Thr Lys Ser Asn Gly Tyr Ser Lys Pro Asn Gly Tyr Thr His Leu<br>                  1695                    1700                  1705 | 5136 |
| aaa ggc tat tca aac cta aac ggt tat tca aaa caa aat ggt tat gca<br>Lys Gly Tyr Ser Asn Leu Asn Gly Tyr Ser Lys Gln Asn Gly Tyr Ala<br>1710                    1715                    1720 | 5184 |
| caa ctc aac ggc cat aga gag cgt aac aat tat tta gat cta aat ggg<br>Gln Leu Asn Gly His Arg Glu Arg Asn Asn Tyr Leu Asp Leu Asn Gly<br>1725                    1730                    1735                  1740 | 5232 |
| cac tca ctg cta aat ggg aat tca gac atc acc aca tca ggg ccc tca<br>His Ser Leu Leu Asn Gly Asn Ser Asp Ile Thr Thr Ser Gly Pro Ser<br>                  1745                    1750                  1755 | 5280 |
| gca aca agc ctt gcc tac gtg atc ttc aca tcc ggc tca acc gga aag<br>Ala Thr Ser Leu Ala Tyr Val Ile Phe Thr Ser Gly Ser Thr Gly Lys<br>                  1760                    1765                  1770 | 5328 |
| ccc aaa gga gtc atg gtc gaa cac cgc agc atc atc cga ctt gca aag<br>Pro Lys Gly Val Met Val Glu His Arg Ser Ile Ile Arg Leu Ala Lys<br>                  1775                    1780                  1785 | 5376 |
| aag aac aga atc ata tcc agg ttc cca tct gta gcc aag gta gct cac<br>Lys Asn Arg Ile Ile Ser Arg Phe Pro Ser Val Ala Lys Val Ala His<br>1790                    1795                    1800 | 5424 |
| ctc tca aac atc gcc ttt gac gcc gcc act tgg gaa atg ttc gca gcc<br>Leu Ser Asn Ile Ala Phe Asp Ala Ala Thr Trp Glu Met Phe Ala Ala<br>1805                    1810                    1815                  1820 | 5472 |

-continued

| | |
|---|---|
| ctt cta aac ggc gga acg ctg gtc tgt atc gac tat atg acc acc ctg<br>Leu Leu Asn Gly Gly Thr Leu Val Cys Ile Asp Tyr Met Thr Thr Leu<br>    1825                                1830                          1835 | 5520 |
| gac agc aaa acg ctc gag gcc gcg ttt gca cga gaa caa atc aac gcc<br>Asp Ser Lys Thr Leu Glu Ala Ala Phe Ala Arg Glu Gln Ile Asn Ala<br>        1840                          1845                        1850 | 5568 |
| gcg tta ctc acg ccc gct ttg ttg aag cag tgc cta gcc aac att ccc<br>Ala Leu Leu Thr Pro Ala Leu Leu Lys Gln Cys Leu Ala Asn Ile Pro<br>    1855                                1860                        1865 | 5616 |
| act acc cta ggc agg ctg agt gca ctc gtt att gga ggt gat agg ctt<br>Thr Thr Leu Gly Arg Leu Ser Ala Leu Val Ile Gly Gly Asp Arg Leu<br>        1870                          1875                        1880 | 5664 |
| gac ggc caa gac gcg atc gca gca cat gcg ctt gtc ggt gct ggc gtg<br>Asp Gly Gln Asp Ala Ile Ala Ala His Ala Leu Val Gly Ala Gly Val<br>1885                          1890                        1895                        1900 | 5712 |
| tat aat gcg tat ggc ccg acc gaa aac gga gtg atc agt acg att tat<br>Tyr Asn Ala Tyr Gly Pro Thr Glu Asn Gly Val Ile Ser Thr Ile Tyr<br>        1905                          1910                        1915 | 5760 |
| aat atc act aaa aac gac tcg ttc atc aac gga gtc ccc atc ggc tgt<br>Asn Ile Thr Lys Asn Asp Ser Phe Ile Asn Gly Val Pro Ile Gly Cys<br>    1920                                1925                        1930 | 5808 |
| gca atc agc aat tcc ggc gcc tac atc aca gac cca gac cag cag ctc<br>Ala Ile Ser Asn Ser Gly Ala Tyr Ile Thr Asp Pro Asp Gln Gln Leu<br>        1935                          1940                        1945 | 5856 |
| gta cct cct ggc gtc atg ggt gaa ctc gtc gtt acc ggt gac ggg ctc<br>Val Pro Pro Gly Val Met Gly Glu Leu Val Val Thr Gly Asp Gly Leu<br>    1950                                1955                        1960 | 5904 |
| gcg cgg ggg tat aca gac cca gca cta gac gcg ggc cgc ttc gtc cag<br>Ala Arg Gly Tyr Thr Asp Pro Ala Leu Asp Ala Gly Arg Phe Val Gln<br>1965                          1970                        1975                        1980 | 5952 |
| atc atg atc aat gac aag gcc gtg agg gcg tac cga acg ggt gac cgg<br>Ile Met Ile Asn Asp Lys Ala Val Arg Ala Tyr Arg Thr Gly Asp Arg<br>        1985                          1990                        1995 | 6000 |
| gca cga tat cgc gta gga gac ggt cag atc gag ttc ttc gga cgc atg<br>Ala Arg Tyr Arg Val Gly Asp Gly Gln Ile Glu Phe Phe Gly Arg Met<br>    2000                                2005                        2010 | 6048 |
| gat cag caa gtc aag atc cga ggt cac cgc att gaa cca gcc gaa gtg<br>Asp Gln Gln Val Lys Ile Arg Gly His Arg Ile Glu Pro Ala Glu Val<br>        2015                          2020                        2025 | 6096 |
| gag cgt gct att ctc gac caa gac tcg gcc cgc gac gcc gtc gtt gtc<br>Glu Arg Ala Ile Leu Asp Gln Asp Ser Ala Arg Asp Ala Val Val Val<br>    2030                                2035                        2040 | 6144 |
| atc cgg cac caa gaa ggt gaa gaa ccg gag atg gtt ggt ttc gtc gcg<br>Ile Arg His Gln Glu Gly Glu Glu Pro Glu Met Val Gly Phe Val Ala<br>2045                          2050                        2055                        2060 | 6192 |
| acc cac ggc gat cac tct gcc gaa caa gag gaa gca gac gac cag gtt<br>Thr His Gly Asp His Ser Ala Glu Gln Glu Glu Ala Asp Asp Gln Val<br>        2065                          2070                        2075 | 6240 |
| gaa ggt tgg aaa gac ttc ttc gag agc aat aca tat gcc gac atg gat<br>Glu Gly Trp Lys Asp Phe Phe Glu Ser Asn Thr Tyr Ala Asp Met Asp<br>    2080                                2085                        2090 | 6288 |
| acc atc ggc cag tct gct ata ggc aac gac ttt acg ggc tgg acg tcc<br>Thr Ile Gly Gln Ser Ala Ile Gly Asn Asp Phe Thr Gly Trp Thr Ser<br>        2095                          2100                        2105 | 6336 |
| atg tac gac ggg agc gag atc aac aag gcc gag atg cag gag tgg ctc<br>Met Tyr Asp Gly Ser Glu Ile Asn Lys Ala Glu Met Gln Glu Trp Leu<br>    2110                                2115                        2120 | 6384 |
| gac gac acc atg cgc aca ctc ctc gat ggc caa gcg ccg ggt cac gta<br>Asp Asp Thr Met Arg Thr Leu Leu Asp Gly Gln Ala Pro Gly His Val | 6432 |

-continued

```
            2125                2130                2135                2140
ctc gaa ata ggc aca ggc agt ggc atg gta ttg ttt aac tta ggg gcc          6480
Leu Glu Ile Gly Thr Gly Ser Gly Met Val Leu Phe Asn Leu Gly Ala
                    2145                2150                2155 ggg cta caa agc tac gta ggt ctt gaa cca tct aga tct gca gcc acg          6528
Gly Leu Gln Ser Tyr Val Gly Leu Glu Pro Ser Arg Ser Ala Ala Thr
            2160                2165                2170 ttt gtt acc aaa gcg atc aat tcc acc cca gct ctt gca gga aag gcc          6576
Phe Val Thr Lys Ala Ile Asn Ser Thr Pro Ala Leu Ala Gly Lys Ala
            2175                2180                2185 gaa gtg cac gtc ggc aca gcg aca gac ata aac cga ctt cgt gga ctt          6624
Glu Val His Val Gly Thr Ala Thr Asp Ile Asn Arg Leu Arg Gly Leu
            2190                2195                2200 cgt ccc gat cta gtt gtg ctc aac tcg gta gtc cag tat ttc ccc acg          6672
Arg Pro Asp Leu Val Val Leu Asn Ser Val Val Gln Tyr Phe Pro Thr
2205                2210                2215                2220 ccc gag tac cta cta gag gtc gtg gag agt ctc gtc cgg att ccg ggc          6720
Pro Glu Tyr Leu Leu Glu Val Val Glu Ser Leu Val Arg Ile Pro Gly
            2225                2230                2235 gtc aag cgc gtg gtc ttc ggc gac ata cga tct cac gcc acg aac aga          6768
Val Lys Arg Val Val Phe Gly Asp Ile Arg Ser His Ala Thr Asn Arg
            2240                2245                2250 cat ttt ctt gct gcc agg gcg ctg cat tcg ctg ggc tcc aag gcg acc          6816
His Phe Leu Ala Ala Arg Ala Leu His Ser Leu Gly Ser Lys Ala Thr
            2255                2260                2265 aaa gat gct ata cgt caa aag atg acg gag atg gaa gag cgc gag gaa          6864
Lys Asp Ala Ile Arg Gln Lys Met Thr Glu Met Glu Glu Arg Glu Glu
            2270                2275                2280 gag ctg ctc gtc gac ccg gcc ttc ttc acg gcg ctg ctg cag ggc cag          6912
Glu Leu Leu Val Asp Pro Ala Phe Phe Thr Ala Leu Leu Gln Gly Gln
2285                2290                2295                2300 ctt gcc gat cga atc aag cac gtc gag atc ctc ccg aag aac atg cgc          6960
Leu Ala Asp Arg Ile Lys His Val Glu Ile Leu Pro Lys Asn Met Arg
            2305                2310                2315 gcc acg aac gag ctg agc gcg tac cgg tat aca gcc gtc att cac gta          7008
Ala Thr Asn Glu Leu Ser Ala Tyr Arg Tyr Thr Ala Val Ile His Val
            2320                2325                2330 cgc ggc cca gag gaa cag tcg cgg ccc gtg tat ccg atc caa gtg aac          7056
Arg Gly Pro Glu Glu Gln Ser Arg Pro Val Tyr Pro Ile Gln Val Asn
            2335                2340                2345 gac tgg atc gac ttt cag gcc tca cgc att gac cgc cgc gcc ctt ctc          7104
Asp Trp Ile Asp Phe Gln Ala Ser Arg Ile Asp Arg Arg Ala Leu Leu
            2350                2355                2360 cga ctc cta cag cgc tcg gca gac gcc gcg acc gtc gcc gtc agc aac          7152
Arg Leu Leu Gln Arg Ser Ala Asp Ala Ala Thr Val Ala Val Ser Asn
2365                2370                2375                2380 atc ccc tac agc aag acg att gta gaa cgc cat gtc gtc gag tcc ctt          7200
Ile Pro Tyr Ser Lys Thr Ile Val Glu Arg His Val Val Glu Ser Leu
            2385                2390                2395 gac aat aac aac agg gag aat acg cat aga gca cca gac ggc gcg gct          7248
Asp Asn Asn Asn Arg Glu Asn Thr His Arg Ala Pro Asp Gly Ala Ala
            2400                2405                2410 tgg atc tcg gcc gtc cgc tcc aag gcc gag cgc tgc acg tcc ctc tcc          7296
Trp Ile Ser Ala Val Arg Ser Lys Ala Glu Arg Cys Thr Ser Leu Ser
            2415                2420                2425 gtg acc gat ctt gtg cag ctc ggg gaa gaa gcc ggc ttt cgc gta gaa          7344
Val Thr Asp Leu Val Gln Leu Gly Glu Glu Ala Gly Phe Arg Val Glu
            2430                2435                2440 gtc agc gca gcg cgg cag tgg tct caa agc ggc gcg ctc gat gcc gtc          7392
```

```
                Val Ser Ala Ala Arg Gln Trp Ser Gln Ser Gly Ala Leu Asp Ala Val
                2445                2450                2455                2460 ttt cac cgc tat aat ttg ccc act caa agc aat agt cgc gtt ctg att          7440
Phe His Arg Tyr Asn Leu Pro Thr Gln Ser Asn Ser Arg Val Leu Ile
            2465                2470                2475 cag ttc cct acc gaa gat ggc cag acg cga aga tcc gcc act ctg aca          7488
Gln Phe Pro Thr Glu Asp Gly Gln Thr Arg Arg Ser Ala Thr Leu Thr
        2480                2485                2490 aac cga cca cta cag cgt ctg cag agc cgt cgg ttc gca tca cag atc          7536
Asn Arg Pro Leu Gln Arg Leu Gln Ser Arg Arg Phe Ala Ser Gln Ile
    2495                2500                2505 cgc gaa cag ctg aag gcc gtg ctc ccg tca tac atg atc ccc tcc cgc          7584
Arg Glu Gln Leu Lys Ala Val Leu Pro Ser Tyr Met Ile Pro Ser Arg
 2510                2515                2520 atc gtg gtc ata gac cag atg cct ctc aat gcc aat ggc aag gtc gac          7632
Ile Val Val Ile Asp Gln Met Pro Leu Asn Ala Asn Gly Lys Val Asp
2525                2530                2535                2540 cgg aaa gaa ctt acc aga agg gcc caa atc gcg ccg aaa tct cag gcg          7680
Arg Lys Glu Leu Thr Arg Arg Ala Gln Ile Ala Pro Lys Ser Gln Ala
            2545                2550                2555 gct ccc gcc aaa ccc gtc aaa cag gtc gat ccg ttc gtc aac ctg gaa          7728
Ala Pro Ala Lys Pro Val Lys Gln Val Asp Pro Phe Val Asn Leu Glu
        2560                2565                2570 gcc att tta tgt gag gag ttc gcg gag gtg ctg ggc atg gaa gtc ggc          7776
Ala Ile Leu Cys Glu Glu Phe Ala Glu Val Leu Gly Met Glu Val Gly
    2575                2580                2585 gtg aac gac cac ttc ttc caa cta ggc gga cac tct ctc ttg gcc acg          7824
Val Asn Asp His Phe Phe Gln Leu Gly Gly His Ser Leu Leu Ala Thr
 2590                2595                2600 aag ctc gtc gcg cgt ctc agt cgt cgg cta aac ggt cgt gtg tct gtg          7872
Lys Leu Val Ala Arg Leu Ser Arg Arg Leu Asn Gly Arg Val Ser Val
2605                2610                2615                2620 agg gat gtg ttc gac cag cct gtg att tcc gac ctc gca gtc acc ctc          7920
Arg Asp Val Phe Asp Gln Pro Val Ile Ser Asp Leu Ala Val Thr Leu
            2625                2630                2635 cgc cag gga ctg acc ttg gaa aac gcc att ccc gca acg ccg gac agc          7968
Arg Gln Gly Leu Thr Leu Glu Asn Ala Ile Pro Ala Thr Pro Asp Ser
        2640                2645                2650 ggg tat tgg gag cag aca atg tcc gca ccg aca acc ccg agc gac gac          8016
Gly Tyr Trp Glu Gln Thr Met Ser Ala Pro Thr Thr Pro Ser Asp Asp
    2655                2660                2665 atg gag gcc gtg cta tgc aag gag ttt gcg gat gtg ctt ggc gtc gaa          8064
Met Glu Ala Val Leu Cys Lys Glu Phe Ala Asp Val Leu Gly Val Glu
 2670                2675                2680 gtc agc gcc acc gac agc ttc ttc gat ctc ggt ggg cat tcc ctc atg          8112
Val Ser Ala Thr Asp Ser Phe Phe Asp Leu Gly Gly His Ser Leu Met
2685                2690                2695                2700 gct acg aag ctc gct gcg cgt att agc cgt cgg cta gat gta ccg gtg          8160
Ala Thr Lys Leu Ala Ala Arg Ile Ser Arg Arg Leu Asp Val Pro Val
            2705                2710                2715 tca atc aaa gac ata ttc gat cac tca gtt cct cta aac ctt gcg agg          8208
Ser Ile Lys Asp Ile Phe Asp His Ser Val Pro Leu Asn Leu Ala Arg
        2720                2725                2730 aag att cgg ctc act caa gca aaa ggc cac gaa gcg acc aat gga gta          8256
Lys Ile Arg Leu Thr Gln Ala Lys Gly His Glu Ala Thr Asn Gly Val
    2735                2740                2745 caa atc gcc aac gac gcc cca ttc caa ctc att tcc gta gaa gat cca          8304
Gln Ile Ala Asn Asp Ala Pro Phe Gln Leu Ile Ser Val Glu Asp Pro
 2750                2755                2760
```

-continued

| | |
|---|---|
| gag ata ttc gtc caa cgt gaa atc gcc cct caa cta caa tgc tca ccc<br>Glu Ile Phe Val Gln Arg Glu Ile Ala Pro Gln Leu Gln Cys Ser Pro<br>2765                2770                2775                2780 | 8352 |
| gag aca atc cta gac gtc tac ccc gcc acg caa atg caa agg gtc ttc<br>Glu Thr Ile Leu Asp Val Tyr Pro Ala Thr Gln Met Gln Arg Val Phe<br>                2785                2790                2795 | 8400 |
| ctc ctc aac cca gta aca gga aag ccg cgc tca cca acg cca ttt cac<br>Leu Leu Asn Pro Val Thr Gly Lys Pro Arg Ser Pro Thr Pro Phe His<br>2800                2805                2810 | 8448 |
| ata gac ttc ccg ccg gac gca gac tgc gcc agc ctg atg cgg gca tgt<br>Ile Asp Phe Pro Pro Asp Ala Asp Cys Ala Ser Leu Met Arg Ala Cys<br>                2815                2820                2825 | 8496 |
| gca tct cta gcg aag cat ttc gat atc ttc agg acg gtg ttc ctc gaa<br>Ala Ser Leu Ala Lys His Phe Asp Ile Phe Arg Thr Val Phe Leu Glu<br>2830                2835                2840 | 8544 |
| gcc aga ggc gaa ctc tac caa gta gtt cta aaa cac gtc gac gtg ccc<br>Ala Arg Gly Glu Leu Tyr Gln Val Val Leu Lys His Val Asp Val Pro<br>2845                2850                2855                2860 | 8592 |
| atc gag atg ctc cag acc gaa gaa aac atc aac agc gcg acc cgg tcg<br>Ile Glu Met Leu Gln Thr Glu Glu Asn Ile Asn Ser Ala Thr Arg Ser<br>                2865                2870                2875 | 8640 |
| ttc ctg gac gta gac gca gaa aaa ccc atc cgg cta ggc cag cca ctg<br>Phe Leu Asp Val Asp Ala Glu Lys Pro Ile Arg Leu Gly Gln Pro Leu<br>2880                2885                2890 | 8688 |
| atc cgc atc gcg ata cta gag aag ccc ggg tcc acg ctg cgc gtc atc<br>Ile Arg Ile Ala Ile Leu Glu Lys Pro Gly Ser Thr Leu Arg Val Ile<br>                2895                2900                2905 | 8736 |
| cta cga tta tcc cac gcc tta tac gac ggc ctg agc cta gag cac atc<br>Leu Arg Leu Ser His Ala Leu Tyr Asp Gly Leu Ser Leu Glu His Ile<br>2910                2915                2920 | 8784 |
| ctg cac tct ctg cac atc ctc ttt ttc ggc ggc agt ctt ccc ccg ccg<br>Leu His Ser Leu His Ile Leu Phe Phe Gly Gly Ser Leu Pro Pro Pro<br>2925                2930                2935                2940 | 8832 |
| ccc aag ttc gcc ggg tac atg caa cac gtc gcg agc agt cgc aga gaa<br>Pro Lys Phe Ala Gly Tyr Met Gln His Val Ala Ser Ser Arg Arg Glu<br>                2945                2950                2955 | 8880 |
| ggc tac gat ttc tgg cgt tcc gtt ctc cga gat tcg tct atg aca gtc<br>Gly Tyr Asp Phe Trp Arg Ser Val Leu Arg Asp Ser Ser Met Thr Val<br>2960                2965                2970 | 8928 |
| atc aaa ggc aac aat aat aca act cca cca cct cct cct caa caa caa<br>Ile Lys Gly Asn Asn Asn Thr Thr Pro Pro Pro Pro Pro Gln Gln Gln<br>                2975                2980                2985 | 8976 |
| tcc acc ccc tcc gga gcc cac cac gcc tcc aaa gta gtc act atc cca<br>Ser Thr Pro Ser Gly Ala His His Ala Ser Lys Val Val Thr Ile Pro<br>2990                2995                3000 | 9024 |
| acc caa gcc aac aca gac agc cgg atc acg cgc gcc acg atc ttc act<br>Thr Gln Ala Asn Thr Asp Ser Arg Ile Thr Arg Ala Thr Ile Phe Thr<br>3005                3010                3015                3020 | 9072 |
| acc gct tgc gca cta atg ctc gcg aaa gaa gac aac tcc agc gac gtc<br>Thr Ala Cys Ala Leu Met Leu Ala Lys Glu Asp Asn Ser Ser Asp Val<br>                3025                3030                3035 | 9120 |
| gtc ttc ggg cgt acg gta tcg ggg cgt caa ggc ctg ccc cta gcc cac<br>Val Phe Gly Arg Thr Val Ser Gly Arg Gln Gly Leu Pro Leu Ala His<br>3040                3045                3050 | 9168 |
| caa aac gtg atc gga cca tgt ctc aac caa gtg ccc gtg cgc gcg cgc<br>Gln Asn Val Ile Gly Pro Cys Leu Asn Gln Val Pro Val Arg Ala Arg<br>                3055                3060                3065 | 9216 |
| ggt tta aac cga gga acc act cac cac cga gaa ctt ctc cgc gag atg<br>Gly Leu Asn Arg Gly Thr Thr His His Arg Glu Leu Leu Arg Glu Met<br>3070                3075                3080 | 9264 |

```
caa gag caa tat ctc aac agt ctc gct ttc gaa act ctc ggg tac gac    9312
Gln Glu Gln Tyr Leu Asn Ser Leu Ala Phe Glu Thr Leu Gly Tyr Asp
3085                3090                3095                3100 gag atc aag gcg cac tgc aca gac tgg ccg gac gtg cca gcg acc gcg    9360
Glu Ile Lys Ala His Cys Thr Asp Trp Pro Asp Val Pro Ala Thr Ala
            3105                3110                3115 agc ttc ggg tgc tgc atc gtg tac cag aac ttc gat tcg cac ccg gac    9408
Ser Phe Gly Cys Cys Ile Val Tyr Gln Asn Phe Asp Ser His Pro Asp
        3120                3125                3130 agc cga gtc gaa gag cag cgg ctg cag atc ggg gtc ttg tcg cgg aac    9456
Ser Arg Val Glu Glu Gln Arg Leu Gln Ile Gly Val Leu Ser Arg Asn
    3135                3140                3145 tac gag gct att aat gag ggg ctc gtg cat gat ctt gtt att gct ggg    9504
Tyr Glu Ala Ile Asn Glu Gly Leu Val His Asp Leu Val Ile Ala Gly
3150                3155                3160 gag tcg gag cct gat ggg gat gat ttg agg gtt act gtt gtg gcg aat    9552
Glu Ser Glu Pro Asp Gly Asp Asp Leu Arg Val Thr Val Val Ala Asn
3165                3170                3175                3180 cgg agg ttg tgc gat gag gaa agg ttg aag agg atg ctg gag gag ctg    9600
Arg Arg Leu Cys Asp Glu Glu Arg Leu Lys Arg Met Leu Glu Glu Leu
            3185                3190                3195 tgt ggg aat att cgg gct ttg gcg ttg gtt tag                        9633
Cys Gly Asn Ile Arg Ala Leu Ala Leu Val
        3200                3205

<210> SEQ ID NO 2
<211> LENGTH: 3210
<212> TYPE: PRT
<213> ORGANISM: Mycelia sterilia

<400> SEQUENCE: 2

Met Ser Asn Met Ala Pro Leu Pro Thr Met Gly Val Glu Gln Gln Ala
 1               5                   10                  15

Leu Ser Leu Ser Cys Pro Leu Leu Pro His Asp Asp Glu Lys His Ser
            20                  25                  30

Asp Asn Leu Tyr Glu Gln Ala Thr Arg His Phe Gly Leu Ser Arg Asp
        35                  40                  45

Lys Ile Glu Asn Val Leu Pro Cys Thr Ser Phe Gln Cys Asp Val Ile
    50                  55                  60

Asp Cys Ala Val Asp Asp Arg Arg His Ala Ile Gly His Val Val Tyr
65                  70                  75                  80

Asp Ile Pro Asn Thr Val Asp Ile Gln Arg Leu Ala Ala Ala Trp Lys
                85                  90                  95

Glu Val Val Arg Gln Thr Pro Ile Leu Arg Thr Gly Ile Phe Thr Ser
            100                 105                 110

Glu Thr Gly Asp Ser Phe Gln Ile Val Leu Lys Glu Gly Cys Leu Pro
        115                 120                 125

Trp Met Tyr Ala Thr Cys Leu Gly Met Lys Gly Ala Val Ile Gln Asp
    130                 135                 140

Glu Ala Val Ala Met Thr Gly Pro Arg Cys Asn Arg Tyr Val Val
145                 150                 155                 160

Leu Glu Asp Pro Ser Thr Lys Gln Arg Leu Leu Ile Trp Thr Phe Ser
                165                 170                 175

His Ala Leu Val Asp Tyr Thr Val Gln Glu Arg Ile Leu Gln Arg Val
            180                 185                 190

Leu Thr Val Tyr Asp Gly Arg Asp Val Glu Cys Pro Arg Ile Lys Asp
        195                 200                 205
```

```
Thr Glu His Val Ser Arg Phe Trp Gln Gln His Phe Glu Gly Leu Asp
    210                 215                 220

Ala Ser Val Phe Pro Leu Leu Pro Ser His Leu Thr Val Cys Asn Pro
225                 230                 235                 240

Asn Ala Arg Ala Glu His His Ile Ser Tyr Thr Gly Pro Val Gln Arg
                245                 250                 255

Lys Trp Ser His Thr Ser Ile Cys Arg Ala Ala Leu Ala Val Leu Leu
                260                 265                 270

Ser Arg Phe Thr His Ser Ser Glu Ala Leu Phe Gly Val Val Thr Glu
            275                 280                 285

Gln Ser His Asn Ser Glu Asp Gln Arg Arg Ser Ile Asp Gly Pro Ala
        290                 295                 300

Arg Thr Val Val Pro Ile Arg Val Leu Cys Ala Pro Asp Gln Tyr Val
305                 310                 315                 320

Ser Asp Val Ile Gly Ala Ile Thr Ala His Glu His Ala Met Arg Gly
                325                 330                 335

Phe Glu His Ala Gly Leu Arg Asn Ile Arg Arg Thr Gly Asp Asp Gly
                340                 345                 350

Ser Ala Ala Cys Gly Phe Gln Thr Val Leu Leu Val Thr Asp Gly Asp
            355                 360                 365

Ala Pro Lys Thr Pro Gly Ser Val Leu His Arg Ser Val Glu Glu Ser
        370                 375                 380

Asp Arg Phe Met Pro Cys Ala Asn Arg Ala Leu Leu Leu Asp Cys Gln
385                 390                 395                 400

Met Ala Gly Asn Ser Ala Ser Leu Val Ala Arg Tyr Asp His Asn Val
                405                 410                 415

Ile Asp Pro Arg Gln Met Ser Arg Phe Leu Arg Gln Leu Gly Tyr Leu
                420                 425                 430

Ile Gln Gln Phe His His Val Asp Leu Pro Leu Val Lys Glu Leu
            435                 440                 445

Asp Val Val Thr Ala Glu Asp Cys Ala Glu Ile Glu Lys Trp Asn Ser
450                 455                 460

Glu Arg Leu Thr Met Gln Asp Ala Leu Ile His Asp Thr Ile Ser Lys
465                 470                 475                 480

Trp Ala Ala Gly Asp Pro Asn Lys Ala Ala Val Phe Ala Trp Asp Gly
                485                 490                 495

Glu Trp Thr Tyr Ala Glu Leu Asp Asn Ile Ser Ser Arg Leu Ala Val
            500                 505                 510

Tyr Ile Gln Ser Leu Asp Leu Arg Pro Gly Gln Ala Ile Leu Pro Leu
        515                 520                 525

Cys Phe Glu Lys Ser Lys Trp Val Val Ala Thr Ile Leu Ala Val Leu
        530                 535                 540

Lys Val Gly Arg Ala Phe Thr Leu Ile Asp Pro Cys Asp Pro Ser Ala
545                 550                 555                 560

Arg Met Ala Gln Val Cys Gln Gln Thr Ser Ala Thr Val Ala Leu Thr
                565                 570                 575

Ser Lys Leu His Asn Thr Thr Leu Arg Ser Val Val Ser Arg Cys Ile
            580                 585                 590

Val Val Asp Asp Asp Leu Leu Arg Ser Leu Pro His Ala Asp Gly Arg
        595                 600                 605

Leu Lys Ala Thr Val Lys Pro Gln Asp Leu Ala Tyr Val Ile Phe Thr
610                 615                 620
```

-continued

```
Ser Gly Ser Thr Gly Glu Pro Lys Gly Ile Met Ile Glu His Arg Gly
625                 630                 635                 640

Phe Val Ser Cys Ala Met Lys Phe Gly Pro Ala Leu Gly Met Asp Glu
            645                 650                 655

His Thr Arg Ala Leu Gln Phe Ala Ser Tyr Ala Phe Gly Ala Cys Leu
                660                 665                 670

Val Glu Val Val Thr Ala Leu Met His Gly Gly Cys Val Cys Ile Pro
            675                 680                 685

Ser Asp Asp Arg Leu Asn Asn Val Pro Glu Phe Ile Lys Arg Ala
    690                 695                 700

Gln Val Asn Trp Val Ile Leu Thr Pro Ser Tyr Ile Gly Thr Phe Gln
705                 710                 715                 720

Pro Glu Asp Val Pro Gly Leu Gln Thr Leu Val Leu Val Gly Glu Pro
                725                 730                 735

Ile Ser Ala Ser Ile Arg Asp Thr Trp Ala Ser Gln Val Arg Leu Leu
                740                 745                 750

Asn Ala Tyr Gly Gln Ser Glu Ser Ser Thr Met Cys Ser Val Thr Glu
            755                 760                 765

Val Ser Pro Leu Ser Leu Glu Pro Asn Asn Ile Gly Arg Ala Val Gly
770                 775                 780

Ala Arg Ser Trp Ile Ile Asp Pro Asp Glu Pro Asp Arg Leu Ala Pro
785                 790                 795                 800

Ile Gly Cys Ile Gly Glu Leu Val Ile Glu Ser Pro Gly Ile Ala Arg
                805                 810                 815

Asp Tyr Ile Ile Ala Pro Pro Asp Lys Ser Pro Phe Leu Leu Ala
                820                 825                 830

Pro Pro Ala Trp Tyr Pro Ala Gly Lys Leu Ser Asn Ala Phe Lys Phe
                835                 840                 845

Tyr Lys Thr Gly Asp Leu Val Arg Tyr Gly Pro Asp Gly Thr Ile Val
850                 855                 860

Cys Leu Gly Arg Lys Asp Ser Gln Val Lys Ile Arg Gly Gln Arg Val
865                 870                 875                 880

Glu Ile Ser Ala Val Glu Ala Ser Leu Arg Arg Gln Leu Pro Ser Asp
                885                 890                 895

Ile Met Pro Val Ala Glu Ala Ile Lys Arg Ser Asp Ser Ser Gly Ser
            900                 905                 910

Thr Val Leu Thr Ala Phe Leu Ile Gly Ser Ser Lys Ser Gly Asp Gly
        915                 920                 925

Asn Gly His Ala Leu Ser Ala Asp Ala Val Ile Leu Asp His Gly
    930                 935                 940

Ala Thr Asn Glu Ile Asn Ala Lys Leu Gln Gln Ile Leu Pro Gln His
945                 950                 955                 960

Ser Val Pro Ser Tyr Tyr Ile His Met Glu Asn Leu Pro Arg Thr Ala
                965                 970                 975

Thr Gly Lys Ala Asp Arg Lys Met Leu Arg Ser Ile Ala Ser Lys Leu
            980                 985                 990

Leu Gly Glu Leu Ser Gln Asn Val Thr Ser Gln Pro Ile Glu Lys His
                995                 1000                1005

Asp Ala Pro Ala Thr Gly Ile Glu Val Lys Leu Lys Glu Leu Trp Phe
    1010                1015                1020

Leu Ser Leu Asn Leu Asn Pro Asn Ser Gln Asp Val Gly Ala Ser Phe
1025                1030                1035                1040

Phe Asp Leu Gly Gly Asn Ser Ile Ile Ala Ile Lys Met Val Asn Met
```

-continued

```
              1045                1050                1055
Ala Arg Ser Ala Gly Ile Ala Leu Lys Val Ser Asp Ile Phe Gln Asn
         1060                1065                1070
Pro Thr Leu Ala Gly Leu Val Asp Val Ile Gly Arg Asp Pro Ala Pro
     1075                1080                1085
Tyr Asn Leu Ile Pro Thr Thr Ala Tyr Ser Gly Pro Val Glu Gln Ser
         1090                1095                1100
Phe Ala Gln Gly Arg Leu Trp Phe Leu Asp Gln Ile Glu Leu Asp Ala
1105                1110                1115                1120
Leu Trp Tyr Leu Leu Pro Tyr Ala Val Arg Met Arg Gly Pro Leu His
             1125                1130                1135
Ile Asp Ala Leu Thr Ile Ala Leu Leu Ala Ile Gln Gln Arg His Glu
         1140                1145                1150
Thr Leu Arg Thr Thr Phe Glu Glu Gln Asp Gly Val Gly Val Gln Val
     1155                1160                1165
Val His Ala Ser Pro Ile Ser Asp Leu Arg Ile Ile Asp Val Ser Gly
     1170                1175                1180
Asp Arg Asn Ser Asp Tyr Leu Gln Leu Leu His Gln Glu Gln Thr Thr
1185                1190                1195                1200
Pro Phe Ile Leu Ala Cys Gln Ala Gly Trp Arg Val Ser Leu Ile Arg
             1205                1210                1215
Leu Gly Glu Asp Asp His Ile Leu Ser Ile Val Met His His Ile Ile
         1220                1225                1230
Ser Asp Gly Trp Ser Ile Asp Ile Leu Arg Arg Glu Leu Ser Asn Phe
     1235                1240                1245
Tyr Ser Ala Ala Leu Arg Gly Ser Asp Pro Leu Ser Val Val Ser Pro
     1250                1255                1260
Leu Pro Leu His Tyr Arg Asp Phe Ser Val Trp Gln Lys Gln Val Glu
1265                1270                1275                1280
Gln Glu Thr Glu His Glu Arg Gln Leu Glu Tyr Trp Val Lys Gln Leu
             1285                1290                1295
Ala Asp Ser Ser Ala Ala Glu Phe Leu Thr Asp Phe Pro Arg Pro Asn
         1300                1305                1310
Ile Leu Ser Gly Glu Ala Gly Ser Val Pro Val Thr Ile Glu Gly Glu
     1315                1320                1325
Leu Tyr Glu Arg Leu Gln Glu Phe Cys Lys Val Glu Gln Met Thr Pro
     1330                1335                1340
Phe Ala Val Leu Leu Gly Ala Phe Arg Ala Thr His Tyr Arg Leu Thr
1345                1350                1355                1360
Gly Ala Glu Asp Ser Ile Ile Gly Thr Pro Ile Ala Asn Arg Asn Arg
             1365                1370                1375
Gln Glu Leu Glu Asn Met Ile Gly Phe Phe Val Asn Thr Gln Cys Met
         1380                1385                1390
Arg Ile Thr Val Asp Gly Asp Asp Thr Phe Glu Ser Leu Val Arg Gln
     1395                1400                1405
Val Arg Thr Thr Ala Thr Ala Ala Phe Glu His Gln Asp Val Pro Phe
     1410                1415                1420
Glu Arg Val Val Thr Ala Leu Leu Pro Arg Ser Arg Asp Leu Ser Arg
1425                1430                1435                1440
Asn Pro Leu Ala Gln Leu Thr Phe Ala Leu His Ser Gln Gln Asp Leu
             1445                1450                1455
Gly Lys Phe Glu Leu Glu Gly Leu Val Ala Glu Pro Val Ser Asn Lys
         1460                1465                1470
```

-continued

```
Val Tyr Thr Arg Phe Asp Val Glu Phe His Leu Phe Gln Glu Ala Gly
    1475                1480                1485

Arg Leu Ser Gly Asn Val Ala Phe Ala Ala Asp Leu Phe Lys Pro Glu
    1490                1495                1500

Thr Ile Ser Asn Val Val Ala Ile Phe Phe Gln Ile Leu Arg Gln Gly
1505                1510                1515                1520

Ile Arg Gln Pro Arg Thr Pro Ile Ala Val Leu Pro Leu Thr Asp Gly
            1525                1530                1535

Leu Ala Asp Leu Arg Ala Met Gly Leu Leu Glu Ile Glu Lys Ala Glu
        1540                1545                1550

Tyr Pro Arg Glu Ser Ser Val Val Asp Val Phe Arg Lys Gln Val Ala
    1555                1560                1565

Ala His Pro His Ala Phe Ala Val Val Asp Ser Ala Ser Arg Leu Thr
    1570                1575                1580

Tyr Ala Asp Leu Asp Arg Gln Ser Asp Gln Leu Ala Thr Trp Leu Gly
1585                1590                1595                1600

Arg Arg Asn Met Thr Ala Glu Thr Leu Val Gly Val Leu Ala Pro Arg
            1605                1610                1615

Ser Cys Gln Thr Val Val Ala Ile Leu Gly Ile Leu Lys Ala Asn Leu
        1620                1625                1630

Ala Tyr Leu Pro Leu Asp Val Asn Cys Pro Thr Ala Arg Leu Gln Thr
    1635                1640                1645

Ile Leu Ser Thr Leu Asn Arg His Lys Leu Val Leu Leu Gly Ser Asn
    1650                1655                1660

Ala Thr Thr Pro Asp Val Gln Ile Pro Asp Val Glu Leu Val Arg Ile
1665                1670                1675                1680

Ser Asp Ile Leu Asp Arg Pro Ile Asn Gly Gln Ala Lys Leu Asn Gly
            1685                1690                1695

His Thr Lys Ser Asn Gly Tyr Ser Lys Pro Asn Gly Tyr Thr His Leu
        1700                1705                1710

Lys Gly Tyr Ser Asn Leu Asn Gly Tyr Ser Lys Gln Asn Gly Tyr Ala
    1715                1720                1725

Gln Leu Asn Gly His Arg Glu Arg Asn Asn Tyr Leu Asp Leu Asn Gly
    1730                1735                1740

His Ser Leu Leu Asn Gly Asn Ser Asp Ile Thr Thr Ser Gly Pro Ser
1745                1750                1755                1760

Ala Thr Ser Leu Ala Tyr Val Ile Phe Thr Ser Gly Ser Thr Gly Lys
            1765                1770                1775

Pro Lys Gly Val Met Val Glu His Arg Ser Ile Ile Arg Leu Ala Lys
        1780                1785                1790

Lys Asn Arg Ile Ile Ser Arg Phe Pro Ser Val Ala Lys Val Ala His
    1795                1800                1805

Leu Ser Asn Ile Ala Phe Asp Ala Ala Thr Trp Glu Met Phe Ala Ala
    1810                1815                1820

Leu Leu Asn Gly Gly Thr Leu Val Cys Ile Asp Tyr Met Thr Thr Leu
1825                1830                1835                1840

Asp Ser Lys Thr Leu Glu Ala Ala Phe Ala Arg Glu Gln Ile Asn Ala
            1845                1850                1855

Ala Leu Leu Thr Pro Ala Leu Leu Lys Gln Cys Leu Ala Asn Ile Pro
        1860                1865                1870

Thr Thr Leu Gly Arg Leu Ser Ala Leu Val Ile Gly Gly Asp Arg Leu
    1875                1880                1885
```

```
Asp Gly Gln Asp Ala Ile Ala Ala His Ala Leu Val Gly Ala Gly Val
    1890                1895                1900

Tyr Asn Ala Tyr Gly Pro Thr Glu Asn Gly Val Ile Ser Thr Ile Tyr
1905                1910                1915                1920

Asn Ile Thr Lys Asn Asp Ser Phe Ile Asn Gly Val Pro Ile Gly Cys
        1925                1930                1935

Ala Ile Ser Asn Ser Gly Ala Tyr Ile Thr Asp Pro Asp Gln Gln Leu
    1940                1945                1950

Val Pro Pro Gly Val Met Gly Glu Leu Val Val Thr Gly Asp Gly Leu
    1955                1960                1965

Ala Arg Gly Tyr Thr Asp Pro Ala Leu Asp Ala Gly Arg Phe Val Gln
    1970                1975                1980

Ile Met Ile Asn Asp Lys Ala Val Arg Ala Tyr Arg Thr Gly Asp Arg
1985                1990                1995                2000

Ala Arg Tyr Arg Val Gly Asp Gly Gln Ile Glu Phe Phe Gly Arg Met
        2005                2010                2015

Asp Gln Gln Val Lys Ile Arg Gly His Arg Ile Glu Pro Ala Glu Val
        2020                2025                2030

Glu Arg Ala Ile Leu Asp Gln Asp Ser Ala Arg Asp Ala Val Val Val
        2035                2040                2045

Ile Arg His Gln Glu Gly Glu Glu Pro Glu Met Val Gly Phe Val Ala
    2050                2055                2060

Thr His Gly Asp His Ser Ala Glu Gln Glu Glu Ala Asp Asp Gln Val
2065                2070                2075                2080

Glu Gly Trp Lys Asp Phe Phe Glu Ser Asn Thr Tyr Ala Asp Met Asp
        2085                2090                2095

Thr Ile Gly Gln Ser Ala Ile Gly Asn Asp Phe Thr Gly Trp Thr Ser
        2100                2105                2110

Met Tyr Asp Gly Ser Glu Ile Asn Lys Ala Glu Met Gln Glu Trp Leu
    2115                2120                2125

Asp Asp Thr Met Arg Thr Leu Leu Asp Gly Gln Ala Pro Gly His Val
        2130                2135                2140

Leu Glu Ile Gly Thr Gly Ser Gly Met Val Leu Phe Asn Leu Gly Ala
2145                2150                2155                2160

Gly Leu Gln Ser Tyr Val Gly Leu Glu Pro Ser Arg Ser Ala Ala Thr
        2165                2170                2175

Phe Val Thr Lys Ala Ile Asn Ser Thr Pro Ala Leu Ala Gly Lys Ala
        2180                2185                2190

Glu Val His Val Gly Thr Ala Thr Asp Ile Asn Arg Leu Arg Gly Leu
        2195                2200                2205

Arg Pro Asp Leu Val Val Leu Asn Ser Val Val Gln Tyr Phe Pro Thr
    2210                2215                2220

Pro Glu Tyr Leu Leu Glu Val Val Glu Ser Leu Val Arg Ile Pro Gly
2225                2230                2235                2240

Val Lys Arg Val Val Phe Gly Asp Ile Arg Ser His Ala Thr Asn Arg
        2245                2250                2255

His Phe Leu Ala Ala Arg Ala Leu His Ser Leu Gly Ser Lys Ala Thr
        2260                2265                2270

Lys Asp Ala Ile Arg Gln Lys Met Thr Glu Met Glu Glu Arg Glu Glu
    2275                2280                2285

Glu Leu Leu Val Asp Pro Ala Phe Phe Thr Ala Leu Leu Gln Gly Gln
    2290                2295                2300

Leu Ala Asp Arg Ile Lys His Val Glu Ile Leu Pro Lys Asn Met Arg
```

-continued

```
           2305                2310                2315                2320
Ala Thr Asn Glu Leu Ser Ala Tyr Arg Tyr Thr Ala Val Ile His Val
           2325                2330                2335
Arg Gly Pro Glu Glu Gln Ser Arg Pro Val Tyr Pro Ile Gln Val Asn
           2340                2345                2350
Asp Trp Ile Asp Phe Gln Ala Ser Arg Ile Asp Arg Arg Ala Leu Leu
           2355                2360                2365
Arg Leu Leu Gln Arg Ser Ala Asp Ala Ala Thr Val Ala Val Ser Asn
           2370                2375                2380
Ile Pro Tyr Ser Lys Thr Ile Val Glu Arg His Val Val Glu Ser Leu
2385                2390                2395                2400
Asp Asn Asn Asn Arg Glu Asn Thr His Arg Ala Pro Asp Gly Ala Ala
           2405                2410                2415
Trp Ile Ser Ala Val Arg Ser Lys Ala Glu Arg Cys Thr Ser Leu Ser
           2420                2425                2430
Val Thr Asp Leu Val Gln Leu Gly Glu Glu Ala Gly Phe Arg Val Glu
           2435                2440                2445
Val Ser Ala Ala Arg Gln Trp Ser Gln Ser Gly Ala Leu Asp Ala Val
           2450                2455                2460
Phe His Arg Tyr Asn Leu Pro Thr Gln Ser Asn Ser Arg Val Leu Ile
2465                2470                2475                2480
Gln Phe Pro Thr Glu Asp Gly Gln Thr Arg Arg Ser Ala Thr Leu Thr
           2485                2490                2495
Asn Arg Pro Leu Gln Arg Leu Gln Ser Arg Arg Phe Ala Ser Gln Ile
           2500                2505                2510
Arg Glu Gln Leu Lys Ala Val Leu Pro Ser Tyr Met Ile Pro Ser Arg
           2515                2520                2525
Ile Val Val Ile Asp Gln Met Pro Leu Asn Ala Asn Gly Lys Val Asp
           2530                2535                2540
Arg Lys Glu Leu Thr Arg Arg Ala Gln Ile Ala Pro Lys Ser Gln Ala
2545                2550                2555                2560
Ala Pro Ala Lys Pro Val Lys Gln Val Asp Pro Phe Val Asn Leu Glu
           2565                2570                2575
Ala Ile Leu Cys Glu Glu Phe Ala Glu Val Leu Gly Met Glu Val Gly
           2580                2585                2590
Val Asn Asp His Phe Phe Gln Leu Gly Gly His Ser Leu Leu Ala Thr
           2595                2600                2605
Lys Leu Val Ala Arg Leu Ser Arg Arg Leu Asn Gly Arg Val Ser Val
           2610                2615                2620
Arg Asp Val Phe Asp Gln Pro Val Ile Ser Asp Leu Ala Val Thr Leu
2625                2630                2635                2640
Arg Gln Gly Leu Thr Leu Glu Asn Ala Ile Pro Ala Thr Pro Asp Ser
           2645                2650                2655
Gly Tyr Trp Glu Gln Thr Met Ser Ala Pro Thr Thr Pro Ser Asp Asp
           2660                2665                2670
Met Glu Ala Val Leu Cys Lys Glu Phe Ala Asp Val Leu Gly Val Glu
           2675                2680                2685
Val Ser Ala Thr Asp Ser Phe Phe Asp Leu Gly Gly His Ser Leu Met
           2690                2695                2700
Ala Thr Lys Leu Ala Ala Arg Ile Ser Arg Arg Leu Asp Val Pro Val
           2705                2710                2715                2720
Ser Ile Lys Asp Ile Phe Asp His Ser Val Pro Leu Asn Leu Ala Arg
           2725                2730                2735
```

```
Lys Ile Arg Leu Thr Gln Ala Lys Gly His Glu Ala Thr Asn Gly Val
        2740                2745                2750

Gln Ile Ala Asn Asp Ala Pro Phe Gln Leu Ile Ser Val Glu Asp Pro
        2755                2760                2765

Glu Ile Phe Val Gln Arg Glu Ile Ala Pro Gln Leu Gln Cys Ser Pro
        2770                2775                2780

Glu Thr Ile Leu Asp Val Tyr Pro Ala Thr Gln Met Gln Arg Val Phe
2785                2790                2795                2800

Leu Leu Asn Pro Val Thr Gly Lys Pro Arg Ser Pro Thr Pro Phe His
        2805                2810                2815

Ile Asp Phe Pro Pro Asp Ala Asp Cys Ala Ser Leu Met Arg Ala Cys
        2820                2825                2830

Ala Ser Leu Ala Lys His Phe Asp Ile Phe Arg Thr Val Phe Leu Glu
        2835                2840                2845

Ala Arg Gly Glu Leu Tyr Gln Val Val Leu Lys His Val Asp Val Pro
        2850                2855                2860

Ile Glu Met Leu Gln Thr Glu Glu Asn Ile Asn Ser Ala Thr Arg Ser
2865                2870                2875                2880

Phe Leu Asp Val Asp Ala Glu Lys Pro Ile Arg Leu Gly Gln Pro Leu
        2885                2890                2895

Ile Arg Ile Ala Ile Leu Glu Lys Pro Gly Ser Thr Leu Arg Val Ile
        2900                2905                2910

Leu Arg Leu Ser His Ala Leu Tyr Asp Gly Leu Ser Leu Glu His Ile
        2915                2920                2925

Leu His Ser Leu His Ile Leu Phe Phe Gly Ser Leu Pro Pro Pro
        2930                2935                2940

Pro Lys Phe Ala Gly Tyr Met Gln His Val Ala Ser Ser Arg Arg Glu
2945                2950                2955                2960

Gly Tyr Asp Phe Trp Arg Ser Val Leu Arg Asp Ser Ser Met Thr Val
        2965                2970                2975

Ile Lys Gly Asn Asn Asn Thr Thr Pro Pro Pro Pro Gln Gln Gln
        2980                2985                2990

Ser Thr Pro Ser Gly Ala His His Ala Ser Lys Val Val Thr Ile Pro
        2995                3000                3005

Thr Gln Ala Asn Thr Asp Ser Arg Ile Thr Arg Ala Thr Ile Phe Thr
        3010                3015                3020

Thr Ala Cys Ala Leu Met Leu Ala Lys Glu Asp Asn Ser Ser Asp Val
3025                3030                3035                3040

Val Phe Gly Arg Thr Val Ser Gly Arg Gln Gly Leu Pro Leu Ala His
        3045                3050                3055

Gln Asn Val Ile Gly Pro Cys Leu Asn Gln Val Pro Val Arg Ala Arg
        3060                3065                3070

Gly Leu Asn Arg Gly Thr Thr His His Arg Glu Leu Leu Arg Glu Met
        3075                3080                3085

Gln Glu Gln Tyr Leu Asn Ser Leu Ala Phe Glu Thr Leu Gly Tyr Asp
        3090                3095                3100

Glu Ile Lys Ala His Cys Thr Asp Trp Pro Asp Val Pro Ala Thr Ala
3105                3110                3115                3120

Ser Phe Gly Cys Cys Ile Val Tyr Gln Asn Phe Asp Ser His Pro Asp
        3125                3130                3135

Ser Arg Val Glu Glu Gln Arg Leu Gln Ile Gly Val Leu Ser Arg Asn
        3140                3145                3150
```

-continued

```
Tyr Glu Ala Ile Asn Glu Gly Leu Val His Asp Leu Val Ile Ala Gly
        3155                3160                3165

Glu Ser Glu Pro Asp Gly Asp Asp Leu Arg Val Thr Val Val Ala Asn
   3170                3175                3180

Arg Arg Leu Cys Asp Glu Glu Arg Leu Lys Arg Met Leu Glu Glu Leu
3185                3190                3195                3200

Cys Gly Asn Ile Arg Ala Leu Ala Leu Val
            3205                3210
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Concensus
      Sequence

<400> SEQUENCE: 3

```
Trp Thr Ser Met Tyr Asp Gly
1               5
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Concensus
      Sequence

<400> SEQUENCE: 4

```
Val Val Gln Tyr Phe Pro Thr
1               5
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene
<220> FEATURE:
<221> NAME/KEY: base
<222> LOCATION: (6)
<223> OTHER INFORMATION: n = a, g, c or t
<220> FEATURE:
<221> NAME/KEY: base
<222> LOCATION: (7)
<223> OTHER INFORMATION: w = a or t
<220> FEATURE:
<221> NAME/KEY: base
<223> OTHER INFORMATION: (8)
<220> FEATURE:
<223> OTHER INFORMATION: s = g or c
<220> FEATURE:
<221> NAME/KEY: base
<222> LOCATION: (9)
<223> OTHER INFORMATION: n = a, g, c or t
<220> FEATURE:
<221> NAME/KEY: base
<222> LOCATION: (15)
<223> OTHER INFORMATION: y = t or c
<220> FEATURE:
<221> NAME/KEY: base
<222> LOCATION: (18)
<223> OTHER INFORMATION: y = t or c

<400> SEQUENCE: 5
tggacnwsna tgtaygaygg                                            20

-continued

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene
<220> FEATURE:
<221> NAME/KEY: base
<222> LOCATION: (3)
<223> OTHER INFORMATION: n = a, g, c or t
<220> FEATURE:
<221> NAME/KEY: base
<222> LOCATION: (6)
<223> OTHER INFORMATION: r = g or a
<220> FEATURE:
<221> NAME/KEY: base
<222> LOCATION: (9)
<223> OTHER INFORMATION: r = g or a
<220> FEATURE:
<221> NAME/KEY: base
<222> LOCATION: (12)
<223> OTHER INFORMATION: y = t or c
<220> FEATURE:
<221> NAME/KEY: base
<222> LOCATION: (15)
<223> OTHER INFORMATION: n = a, g, c or t
<220> FEATURE:
<221> NAME/KEY: base
<222> LOCATION: (18)
<223> OTHER INFORMATION: n = a, g, c or t

<400> SEQUENCE: 6
gtnggraart aytgnacnac                                              20

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 7
gcggaattaa ccctcactaa agggaacgaa                                   30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 8
gcgtaatacg actcactata gggcgaagaa                                   30

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 9
agcatcggat cctaacaatg ggcgttgagc agcaagccct a                      41

<210> SEQ ID NO 10

```
<211> LENGTH: 21
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 10
tttgcttcgt actcgggtcc t                                          21

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 11
agcatcggat cctaacaatg tcaaacatgg caccactccc ta                   42

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 12
gcatcgcgat actagagaag                                            20

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 13
agcatcgaat tcggatccct aaaccaacgc caaagcccga at                   42

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 14
ctcaaaccag gaactctttc                                            20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 15
gacatgtgga aaccacattt tg                                         22
```

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 16
ggggaattcg tgggtggtga tatcatggc                                29

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 17
gggggatcct tgatgggttt tggg                                     24

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 18
gggggatcct aaactcccat ctatagc                                  27

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Primer for
      Abp1 Gene

<400> SEQUENCE: 19
gggtctagac gactcattgc agtgagtgg                                29

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer for
      Abp1 Gene Promoter

<400> SEQUENCE: 20
tgatatgctg gagcttccct                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer for
      Cyclic Depsipeptide Synthetase Gene

<400> SEQUENCE: 21
gcacaacctc tttccaggct                                          20